United States Patent
Baudin et al.

(10) Patent No.: US 6,906,113 B2
(45) Date of Patent: Jun. 14, 2005

(54) SURFACE-ACTIVE PHOTOINITIATORS

(75) Inventors: Gisèle Baudin, Allschwil (CH); Tunja Jung, Rheinfelden-Herten (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 108 days.

(21) Appl. No.: 10/343,617

(22) PCT Filed: Aug. 7, 2001

(86) PCT No.: PCT/EP01/09122

§ 371 (c)(1),
(2), (4) Date: Feb. 3, 2003

(87) PCT Pub. No.: WO02/14326

PCT Pub. Date: Feb. 21, 2002

(65) Prior Publication Data

US 2004/0014832 A1 Jan. 22, 2004

(30) Foreign Application Priority Data

Aug. 14, 2000 (EP) .............................................. 00810721

(51) Int. Cl.$^7$ ........................... C08F 2/46; C07D 307/93
(52) U.S. Cl. ................................ 522/37; 522/8; 522/6; 522/7; 522/35; 522/905; 522/172; 522/33; 522/182; 522/36; 522/39; 522/42; 522/104; 522/113; 522/114; 522/116; 522/117; 522/126; 522/129; 522/130; 522/134; 522/135; 522/136; 522/139; 522/138; 560/9; 560/51; 560/53; 549/465; 427/487; 427/493; 427/496; 427/508

(58) Field of Search .............................. 522/8, 6, 7, 35, 522/37, 905, 172, 33, 182, 36, 39, 42, 104, 113, 114, 116, 117, 126, 129, 130, 134, 135, 136, 139, 138; 549/465; 560/9, 51, 53; 428/411.1; 427/487, 493, 496, 508

(56) References Cited

U.S. PATENT DOCUMENTS

| 4,987,159 A | * | 1/1991 | Li Bassi et al. .............. 522/36 |
| 6,048,660 A | * | 4/2000 | Leppard et al. ........... 430/270.1 |
| 6,562,464 B1 | * | 5/2003 | Schwalm et al. ......... 428/411.1 |

FOREIGN PATENT DOCUMENTS

| DE | 19913353 | 9/2000 |
| EP | 0128321 | 12/1984 |
| EP | 0129443 | 12/1984 |
| EP | 0161830 | 11/1985 |
| EP | 0162572 | 11/1985 |
| WO | 97/49768 | 12/1997 |
| WO | 98/33761 | 8/1998 |

* cited by examiner

Primary Examiner—James J. Seidleck
Assistant Examiner—Sanza L. McClendon
(74) Attorney, Agent, or Firm—Shiela A. Loggins

(57) ABSTRACT

Compounds of formula Ia, Ib and Ic, (Ic), in which R, $R_1$ and $R_2$ are e.g. phenyl, naphthyl, anthracyl, phenanthryl or a heterocyclic radical, are suitable as photoinitiators which accumulate at the surface of coatings.

14 Claims, No Drawings

SURFACE-ACTIVE PHOTOINITIATORS

The invention relates to surface-active photoinitiators, to a process for producing stable scratch-resistant coatings using such photoinitiators, and to compositions comprising novel surface-active photoinitiators.

For improving the miscibility (compatibility) of photoinitiators with silicone substrates to be crosslinked photochemically, WO 97/49768, U.S. Pat. Nos. 5,776,658, 4,391,963 and EP-A 088842, for example, propose photoinitiators, for example of the hydroxyketone, aminoketone, benzoin ether, benzophenone or thioxanthone type, which have been modified with silyl radicals, including in particular polymeric silyl radicals. Additionally, the patents U.S. Pat. Nos. 4,536,265, 4,534,838 and EP-A 162572 describe a wide variety of photoinitiator structures provided with organopolysiloxane radicals. These compounds are, for example, derived from dialkoxyacetophenones and have increased solubility in silicone substrates. U.S. Pat. No. 4,507,187 discloses diketo photoinitiators containing silyl groups as photoinitiators of good solubility in silicone polymers, and also the polymers obtained with these initiators. U.S. Pat. No. 4,477,326 describes self-polymerizing siloxane polymers containing photoinitiator units as groups which trigger the polymerization reaction. Polymeric photoinitiators with siloxane radicals are specified in U.S. Pat. No. 4,587,276.

A. Kolar, H. F. Gruber and G. Greber report in J.M.S. Pure Appl. Chem. A31 (3) (1994), 305–318 on reactive, silyl-derivatized α-hydroxy ketone photoinitiators. The literature references mentioned deal in particular with the solution of the problem of improving the miscibility of the photoinitiators with the substrate that is to be polymerized, i.e. of making the distribution of the initiator within the substrate as homogeneous as possible. WO 98/00456 proposes certain coating compositions and also a curing method by which improved coating surface properties are achieved.

Phenylglyoxalate esters having long alkyl chains on the aromatic ring are described in JCS Perkin Trans. I (1996) 114, in JACS (1992) 121 2657–61 and in EP-A 0 517 301

Within the coatings industry a search is on for new, energy-saving, emissions-minimizing curing mechanisms and applications for preparing stable scratch-resistant coatings. A particular requirement is to improve the surface of coatings, particularly with regard to hardness, resistance and gloss properties.

It has now been found that the desired properties may be achieved when certain photoinitiators are used in the coatings that are to be cured. For this purpose, the photoinitiator is not distributed as homogeneously as possible in the formulation to be cured but instead accumulates specifically at the surface of the coating to be cured; in other words, there is a specific orientation of the initiator towards the surface of the formulation. To achieve this it is necessary to use specially equipped photoinitiators.

The invention provides surface-active photoinitiator compounds of the formula Ia, Ib or Ic

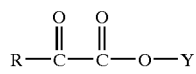
(Ia)

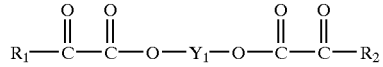
(Ib)

-continued

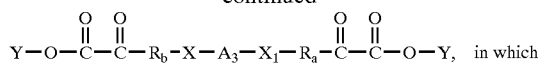
in which

R, $R_1$ and $R_2$ independently of one another are a radical of the formula II

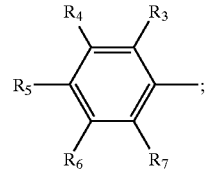
(II)

or

R, $R_1$ and $R_2$ are naphthyl, anthracyl, phenanthryl or a heterocyclic radical, the radicals naphthyl, anthracyl, phenanthryl and the heterocyclic radical being unsubstituted or substituted by A-X—, $A_1$-$X_1$—, $A_2$-$X_2$—, $C_1$–$C_8$alkyl, phenyl, $OR_8$, $SR_9$ and/or $NR_{10}R_{11}$, where the substituents $OR_8$, $SR_9$ and $NR_{10}R_{11}$ may form 5- or 6-membered rings via the radicals $R_8$, $R_9$, $R_{10}$ and/or $R_{11}$ with further substituents on the naphthyl, anthracyl or phenanthryl ring or on the heterocycle or with one of the carbon atoms of the naphthyl, anthracyl or phenanthryl ring or with one of the carbon atoms of the heterocycle; with the proviso that at least one substituent A-X—, $A_1$-$X_1$— or $A_2$-$X_2$— is present in the radical R or in at least one of the radicals $R_1$ or $R_2$;

$R_3$, $R_4$, $R_5$, $R_6$ and $R_7$ independently of one another are hydrogen; A-X—, $A_1$-$X_1$—, $A_2$-$X_2$—; unsubstituted $C_1$–$C_{12}$alkyl or $C_1$–$C_{12}$alkyl substituted by OH, $C_1$–$C_4$alkoxy, phenyl, naphthyl, halogen, CN and/or —O(CO)$R_{12}$; or are $C_2$–$C_{12}$alkyl interrupted by one or more non-successive oxygen atoms; or $R_3$, $R_4$, $R_5$, $R_6$ and $R_7$ are halogen, $OR_8$, $SR_9$, $NR_{10}R_{11}$, unsubstituted or $C_1$–$C_4$alkyl- and/or $C_1$–$C_4$alkoxy-substituted phenyl, where the substituents $OR_8$, $SR_9$, $NR_{10}R_{11}$ may form 5- or 6-membered rings via the radicals $R_8$, $R_9$, $R_{10}$ and/or $R_{11}$ with further substituents on the phenyl ring or one of the carbon atoms of the phenyl ring;

with the proviso that at least one radical $R_3$, $R_4$, $R_5$, $R_6$ or $R_7$ is A-X—, $A_1$-$X_1$—, or $A_2$-$X_2$—;

$R_8$ and $R_9$ independently of one another are hydrogen; unsubstituted $C_1$–$C_{12}$alkyl or $C_1$–$C_{12}$alkyl substituted by OH, $C_1$–$C_4$alkoxy, phenyl, phenoxy and/or —O(CO)$R_{12}$; or are $C_2$–$C_{12}$alkyl interrupted by one or more non-successive oxygen atoms; or are unsubstituted phenyl, $C_3$–$C_6$alkenyl, cyclopentyl, cyclohexyl or naphthyl; or are $C_1$–$C_4$alkoxy-, phenyl- and/or $C_1$–$C_4$alkyl-substituted phenyl, $C_3$–$C_6$alkenyl, cyclopentyl, cyclohexyl or naphthyl;

$R_{10}$ and $R_{11}$ independently of one another are hydrogen; unsubstituted $C_1$–$C_{12}$alkyl or $C_1$–$C_{12}$alkyl substituted by OH, $C_1$–$C_4$alkoxy and/or phenyl; or are $C_2$–$C_{12}$alkyl interrupted by one or more non-successive oxygen atoms; or are phenyl, —(CO)$R_{12}$ or SO$_2R_{13}$; or $R_{10}$ and $R_{11}$, together with the nitrogen atom to which they are attached, form a 5-, 6- or 7-membered ring which is uninterrupted or interrupted by —O— or —$NR_{14}$—;

$R_{12}$ is $C_1$–$C_8$alkyl; unsubstituted phenyl or phenyl substituted by $C_1$–$C_4$alkyl and/or $C_1$–$C_4$alkoxy;

$R_{13}$ is $C_1$–$C_{12}$alkyl, unsubstituted phenyl or phenyl substituted by $C_1$–$C_4$alkyl;

$R_{14}$ is hydrogen; unsubstituted $C_1$–$C_8$alkyl; $C_1$–$C_8$alkyl substituted by OH or $C_{1-C_4}$alkoxy; unsubstituted phenyl; or phenyl substituted by OH, $C_1$–$C_4$alkyl or $C_1$–$C_4$alkoxy;

$R_a$ and $R_b$ independently of one another are phenylene, naphthylene, anthracylene, phenanthrylene or a divalent heterocyclic radical, these radicals being unsubstituted or substituted by A-X—, $A_1$-$X_1$—, $A_2$-$X_2$—, $C_1$–$C_8$alkyl, phenyl, $OR_8$, $SR_9$ and/or $NR_{10}R_{11}$, where the substituents $OR_8$, $SR_9$ and $NR_{10}R_{11}$ may form 5- or 6-membered rings via the radicals $R_8$, $R_9$, $R_{10}$ and/or $R_{11}$ with further substituents on the phenylene, naphthylene, anthracylene or phenanthrylene ring or on the divalent heterocycle or with one of the carbon atoms of the naphthylene, anthracylene or phenanthrylene ring or of the divalent heterocycle;

A, $A_1$ and $A_2$ independently of one another are a surface-active radical of the formula III

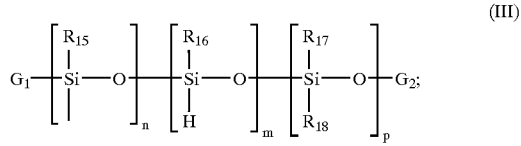

(III)

in which the units IIIa1, IIIa2, IIIb and/or IIIc

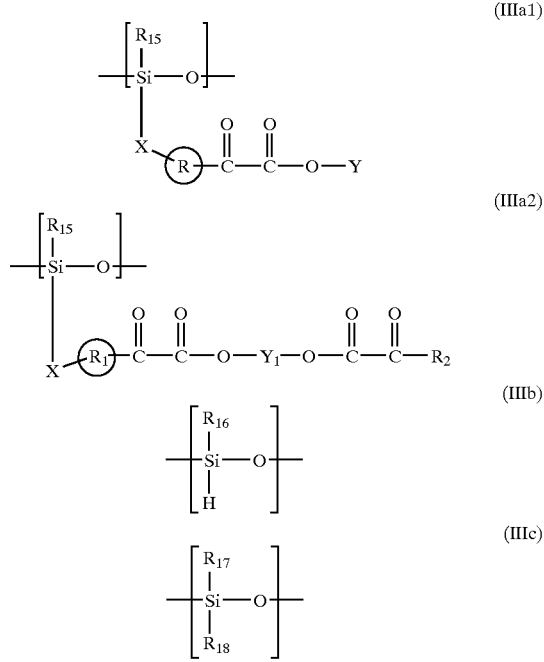

(IIIa1)

(IIIa2)

(IIIb)

(IIIc)

are distributed randomly or in blocks and in which the circle is intended to show that an aromatic radical R or $R_1$ as defined above is a divalent radical and is substituted via the bridges X or $X_1$ with the corresponding silyl radical; or A, $A_1$ and $A_2$ are a surface-active radical $A_0$; where $A_0$ is $C_6$–$C_{30}$alkyl, $C_6$–$C_{30}$alkenyl, $C_6$–$C_{30}$alkynyl, $C_6$–$C_{30}$aralkyl, $C_6$–$C_{30}$alkyl-(CO)—, $C_6$–$C_{30}$alkenyl-(CO)—, $C_6$–$C_{30}$alkynyl-(CO)—, $C_6$–$C_{30}$aralkyl-(CO)—, $C_6$–$C_{30}$alkyl-Si($R_{15}$)($R_{16}$)—, $C_6$–$C_{30}$alkenyl-Si($R_{15}$)($R_{16}$)—, $C_6$–$C_{30}$alkynyl-Si($R_{15}$)($R_{16}$)—, these radicals being unsubstituted or substituted by OH, $C_1$–$C_4$alkoxy, phenyl, naphthyl, halogen, CN, $SR_9$, $NR_{10}R_{11}$ and/or —O(CO)$R_{12}$ and these radicals being uninterrupted or interrupted by one or more —O—, —S— or —$NR_{14}$—;

n is a number from 1 to 1000 or, if the siloxane starting material is a mixture of oligomeric siloxanes, n may alternatively be less than 1 but greater than 0;

m is a number from 0 to 100;

p is a number 0–10 000;

$A_3$ is a radical of the formula III in which n is from 2 to 1000; or $A_3$ is a surface-active radical $A_4$, where $A_4$ is $C_6$–$C_{30}$alkylene, $C_6$–$C_{30}$alkenylene, $C_6$–$C_{30}$alkynylene, $C_6$–$C_{30}$aralkylene, $C_6$–$C_{30}$alkylene-(CO)—, $C_6$–$C_{30}$alkenylene-(CO)—, $C_6$–$C_{30}$alkynylene-(CO)—, $C_6$–$C_{30}$aralkylene-(CO)—, —(CO)—$C_6$–$C_{30}$alkylene-(CO)—, —(CO)—$C_6$–$C_{30}$alkenylene-(CO)—, —(CO)—$C_6$–$C_{30}$alkynylene-(CO)—, —(CO)—$C_6$–$C_{30}$aralkylene-(CO)—, $C_6$–$C_{30}$alkylene-Si($R_{15}$)($R_{16}$)—, $C_6$–$C_{30}$alkenylene-Si($R_{15}$)($R_{16}$)—, $C_6$–$C_{30}$alkynylene-Si($R_{15}$)($R_{16}$)—, —Si($R_{15}$)($R_{16}$)—$C_6$–$C_{30}$alkylene-Si($R_{15}$)($R_{16}$)—, —Si($R_{15}$)($R_{16}$)—$C_6$–$C_{30}$alkenylene-Si($R_{15}$)($R_{16}$)—, —Si($R_{15}$)($R_{16}$)—$C_6$–$C_{30}$alkynylene-Si($R_{15}$)($R_{16}$)—, these radicals being unsubstituted or substituted by OH, $C_1$–$C_4$alkoxy, phenyl, naphthyl, halogen, CN, $SR_9$, $NR_{10}R_{11}$ and/or —O(CO)$R_{12}$ and these radicals being uninterrupted or interrupted by one or more —O—, —S— or —$NR_{14}$—;

$G_1$ is $C_1$–$C_{18}$alkyl or a radical of the formula

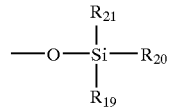

$G_2$ is $C_1$–$C_{18}$alkyl or a radical of the formula

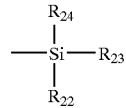

with the proviso that, if $G_2$=alkyl, the radical $G_2$ is attached directly to the silicon atom without an oxygen bridge; or $G_1$ and $G_2$ together are a single bond;

$R_{15}$, $R_{16}$, $R_{17}$, $R_{19}$, $R_{20}$, $R_{21}$, $R_{22}$, $R_{23}$ and $R_{24}$ independently of one another are $C_1$–$C_{18}$alkyl, phenyl, $C_2$–$C_6$-hydroxyalkyl, $C_2$–$C_6$-aminoalkyl or $C_5$–$C_8$cycloalkyl;

$R_{18}$ is unsubstituted $C_1$–$C_{18}$alkyl, $C_5$–$C_8$cycloalkyl; or is $C_1$–$C_{18}$alkyl substituted by hydroxyl, $C_1$–$C_{12}$alkoxy, halogen, $C_3$–$C_8$cycloalkyl and/or N($R_{10}$)($R_{11}$); or is unsubstituted phenyl or phenyl substituted by $C_1$–$C_{12}$alkyl, $C_1$–$C_{12}$alkoxy, halogen, hydroxyl and/or N($R_{10}$)($R_{11}$);

X, $X_1$ and $X_2$ if A, $A_1$, $A_2$ and $A_3$ are a radical of the formula III, independently of one another are a single bond, $C_1$–$C_{10}$alkylene, $C_2$–$C_{10}$alkenylene, $C_2$–$C_{10}$alkynylene, —($CH_2$)$_a$—O—, —O—($CH_2$)$_a$—, —O—($CH_2$)$_a$—O—, —($CH_2$)$_a$—O—($CH_2$)$_b$—, —($CH_2$)$_a$—O—($CH_2$)$_b$—O—, —($CH_2$)$_a$—$NR_{14}$—($CH_2$)$_b$—, —($CH_2$)$_a$—$NR_{14}$—, —($CH_2$)$_a$—O—($CH_2$)$_b$—$NR_{14}$—($CH_2$)$_c$—, —($CH_2$)$_a$—O—($CH_2$)$_b$—$NR_{14}$—, —($C_2$–$C_{10}$alkenylene)-O—($CH_2$)$_a$—, —($C_2$–$C_{10}$alkenylene)-O—, —($C_2$–$C_{10}$alkynylene)-O—($CH_2$)$_a$—, —($C_2$–$C_{10}$alkynylene)-O—, —($C_2$–$C_{10}$alkenylene)-O—($CH_2$)$_a$—O—, —($C_2$–$C_{10}$alkynylene)-O—($CH_2$)$_a$—O—, —($C_2$–$C_{10}$alkenylene)-$NR_{14}$—($CH_2$)$_a$—, —($C_2$–$C_{10}$alkenylene)-$NR_{14}$—, —($C_2$–$C_{10}$alkynylene)-$NR_{14}$—($CH_2$)$_a$—, —($C_2$–$C_{10}$alkynylene)-$NR_{14}$—, —($C_2$–$C_{10}$alkenylene)-O—($CH_2$)$_a$—$NR_{14}$— or —($C_2$–$C_{10}$alkynylene)-O—($CH_2$)$_a$—$NR_{14}$—; and X, $X_1$ and $X_2$ if A, $A_1$ or $A_2$ have the definition of $A_0$ or $A_3$ has the definition of $A_4$, independently of one another are a single bond, —O—, —S— or —$NR_{14}$—;

a, b and c independently of one another are a number from 0 to 10; but with the proviso that they are at least 1 if the methylene group in question is between two oxygen atoms or between one oxygen atom and one nitrogen atom;

Y is hydrogen; unsubstituted $C_1$–$C_{20}$alkyl or $C_1$–$C_{20}$alkyl substituted by a group A-X—; unsubstituted $C_2$–$C_{18}$alkenyl or $C_2$–$C_{18}$alkenyl substituted by a group A-X—; unsubstituted $C_2$–$C_{18}$alkynyl or $C_2$–$C_{18}$alkynyl substituted by a group A-X—; or Y is phenyl, naphthyl, anthracyl or phenanthryl, these radicals being unsubstituted or substituted by one or more groups A-X— and/or $C_1$–$C_{12}$alkyl; or Y is $C_1$–$C_4$alkyl which is substituted by phenyl, naphthyl, anthracyl, phenanthryl and if desired additionally by a group A-X—; or Y is the salt radical of the respective glyoxalic acid;

$Y_1$ is unsubstituted $C_1$–$C_{12}$alkylene or $C_1$–$C_{12}$alkylene substituted by a group $A_1$-$X_1$—; unsubstituted $C_4$–$C_8$alkenylene or $C_4$–$C_8$alkenylene substituted by a group $A_1$-$X_1$—; unsubstituted $C_4$–$C_8$alkynylene or $C_4$–$C_8$alkynylene substituted by a group $A_1$-$X_1$—; unsubstituted cyclohexylene or cyclohexylene substituted by a group $A_1$-$X_1$—; $C_4$–$C_{40}$alkylene which is interrupted one or more times by —O—, —S— or —$NR_{25}$— and which is unsubstituted or substituted by a group $A_1$-$X_1$—; or $Y_1$ is unsubstituted phenylene or phenylene substituted by a group $A_1$-$X_1$—; or $Y_1$ is a radical of the formula V, VI, VII, VIII, IX, X, XI, XII, XIII, XIV or XV

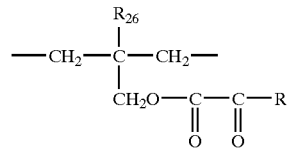

(V)

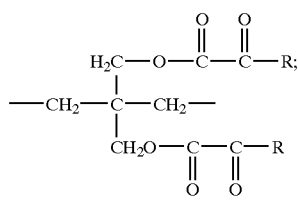

(VI)

—$CH_2CH(OH)CH_2O$—$Y_2$—$OCH_2CH(OH)CH_2$— (VII)
—$CH_2CH(OH)CH_2$— (VIII)

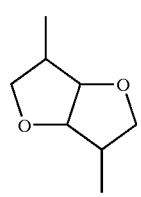

(IX)

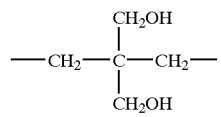

(X)

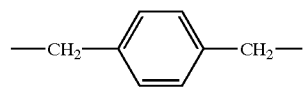

(XI)

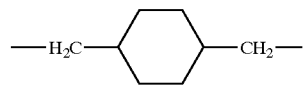

(XII)

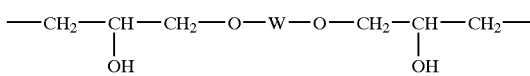

(XIII)

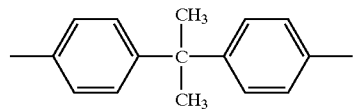

(XIV)

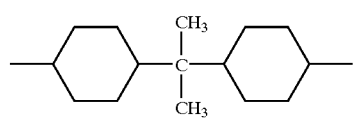

(XV)

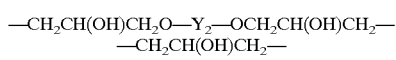

where the radicals of the formula V, VI, VII, VIII, IX, X, XI, XII, XIII, XIV or XV are unsubstituted or substituted by a group $A_1$—$X_1$—;
$Y_2$ is $Y_1$ with the exception of the formula VII;
$R_{25}$ is hydrogen, $C_1$—$C_{12}$alkyl or phenyl; and
$R_{26}$ is hydrogen, $CH_2OH$ or $C_1$—$C_4$alkyl;
W is $C_1$–$C_{10}$alkylene; and
R is as defined above.

$C_1$–$C_{20}$Alkyl is linear or branched and is for example $C_1$–$C_{18}$-, $C_1$–$C_{12}$-, $C_1$–$C_8$-, $C_1$–$C_6$- or $C_1$–$C_4$alkyl. Examples are methyl, ethyl, propyl, isopropyl, n-butyl, sec-butyl, iso-butyl, tert-butyl, pentyl, hexyl, heptyl, 2,4,4-trimethylpentyl, 2-ethylhexyl, octyl, nonyl, decyl, undecyl, dodecyl, tetradecyl, pentadecyil, hexadecyl, heptadecyl, octadecyl, nonadecyl or eicosyl.

$C_1$–$C_{18}$Alkyl, $C_1$–$C_{12}$alkyl, $C_1$–$C_8$alkyl and $C_1$–$C_4$alkyl have the same definitions as indicated above but with the corresponding number of carbon atoms.

$C_6$–$C_{30}$Alkyl is likewise linear and branched and is for example $C_6$–$C_{24}$-, $C_6$–$C_{12}$-, $C_{10}$–$C_{30}$-, $C_{10}$–$C_{24}$-, $C_{12}$–$C_{30}$alkyl. Examples are hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl, eicosyl, henicosyl, docosyl, tricosyl, tetracosyl, pentacosyl, hexacosyl, heptacosyl, octacosyl or triacontyl.

$C_2$–$C_{12}$Alkyl interrupted by one or more oxygen atoms is for example interrupted 1–9, 1–7 or 1 or 2 times by —O—. Where the radicals are interrupted by two or more —O—, the oxygen atoms are each separate from one another by at least one methylene group. This results, for example, in structural units such as —$CH_2$—O—$CH_3$, —$CH_2CH_2$—O—$CH_2CH_3$, —[$CH_2CH_2O$]$_y$—$CH_3$, where y=1–9, —($CH_2CH_2O$)$_7CH_2CH_3$, —$CH_2$—$CH(CH_3)$—O—$CH_2$—$CH_2CH_3$ or —$CH_2$—$CH(CH_3)$—O—$CH_2CH_3$.

C$_2$–C$_6$Hydroxyalkyl is C$_2$–C$_6$alkyl substituted by OH. The alkyl radical is linear or branched and may have the definitions indicated above (with the corresponding number of carbon atoms).

C$_2$–C$_6$Aminoalkyl is C$_2$–C$_6$alkyl substituted by NH$_2$. The alkyl radical is linear or branched and may have the definitions indicated above (with the corresponding number of carbon atoms).

C$_1$–C$_{12}$Alkoxy stands for linear or branched radicals and is for example C$_1$–C$_{10}$-, C$_1$–C$_8$-, C$_1$–C$_6$- or C$_1$–C$_4$alkoxy. Examples are methoxy, ethoxy, propoxy, isopropoxy, n-butyloxy, sec-butyloxy, iso-butyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, iso-butyloxy, tert-butyloxy, preferably methoxy. C$_1$–C$_4$Alkoxy is likewise linear or branched and has, for example, the definitions indicated above with the corresponding number of carbon atoms.

C$_3$–C$_8$Cycloalkyl is linear or branched alkyl containing at least one ring, for example cyclopropyl, cyclopentyl, methyl-cyclopentyl, cyclohexyl, methyl- or dimethyl-cyclohexyl, or cyclooctyl, especially cyclopentyl and cyclohexyl.

C$_5$–C$_8$Cycloalkyl has the definitions indicated above with the corresponding number of carbon atoms.

C$_2$–C$_{18}$Alkenyl may be mono- or polyunsaturated and may be linear or branched and is for example C$_1$–C$_{12}$-, C$_2$–C$_8$-, C$_4$–C$_{12}$alkenyl. Examples are vinyl, allyl, methallyl, 1,1-dimethylallyl, 1-butenyl, 2-butenyl, 1,3-pentadienyl, 1-hexenyl, heptenyl, 2,4,4-trimethylpentenyl, 2-ethylhexenyl, octenyl, nonenyl, decenyl, undecenyl, dodecenyl, tetradecenyl, pentadecenyl, hexadecenyl, heptadecenyl or octadecenyl.

C$_3$–C$_6$Alkenyl may be mono- or polyunsaturated and may be linear or branched and is for example C$_3$–C$_4$alkenyl. Examples are allyl, methallyl, 1,1-dimethylallyl, 1-butenyl, 2-butenyl, 1,3-pentadienyl or 1-hexenyl, especially allyl.

C$_6$–C$_{30}$Alkenyl is likewise linear or branched and mono- or polyunsaturated and is for example C$_6$–C$_{24}$-, C$_6$–C$_{12}$-, C$_{10}$–C$_{30}$-, C$_{10}$–C$_{24}$-, C$_{12}$–C$_{30}$alkenyl. Examples are hexenyl, heptenyl, 2,4,4-trimethylpentenyl, 2-ethylhexenyl, octenyl, nonenyl, decenyl, undecenyl, dodecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl or triacontenyl.

C$_2$–C$_{18}$Alkynyl is linear or branched and mono- or polyunsaturated and is for example C$_6$–C$_{18}$-, C$_2$–C$_{12}$-, C$_2$–C$_{10}$-, C$_2$–C$_8$-, C$_2$–C$_4$alkynyl. Examples are ethynyl, propynyl, 1-butynyl, 2-butynyl, pentynyl, hexynyl, heptynyl, 2,4,4-trimethylpentynyl, 2-ethylhexynyl or octynyl.

C$_6$–C$_{30}$Alkynyl is linear or branched and mono- or polyunsaturated and is for example C$_6$–C$_{24}$-, C$_6$–C$_{12}$-, C$_{10}$–C$_{30}$-, C$_{10}$–C$_{24}$-, C$_{12}$–C$_{30}$alkynyl. Examples are hexynyl, heptynyl, 2,4,4-trimethylpentynyl, 2-ethylhexynyl, octynyl, nonynyl, decynyl, undecynyl, dodecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl or triacontynyl.

C$_6$–C$_{30}$Aralkyl is alkyl substituted by an aromatic radical. Examples are phenyl-C$_1$–C$_{24}$alkyl, naphthyl-C$_1$–C$_{20}$alkyl, anthryl-C$_1$–C$_{16}$alkyl, phenanthryl-C$_1$–C$_{16}$alkyl, the corresponding alkyl radical C$_1$–C$_{24}$, C$_1$–C$_{20}$, C$_1$–C$_{16}$ in each case being substituted by the respective corresponding aromatic radical phenyl, naphthyl, anthryl or phenanthryl. The alkyl radicals are linear or branched and may have the definition indicated above. Examples are benzyl, phenylethyl, α-methylbenzyl, phenylpentyl, phenylhexyl or α,α-dimethylbenzyl, especially benzyl, naphthylmethyl, naphthylethyl, naphthylpropyl or naphthyl-1-methylethyl, in particular naphthylmethyl. The alkyl unit may be in either 1 position or 2 position on the naphthyl ring.

Halogen is fluorine, chlorine, bromine and iodine, especially chlorine and bromine, preferably fluorine.

Substituted phenyl is substituted from one to five times, for example once, twice or three times, especially once or twice, on the phenyl ring.

A heterocyclic radical in this context includes not only aliphatic but also aromatic rings containing one or more, especially one or two, heteroatoms. Fused ring systems are included. Examples of suitable heteroatoms include particularly O, N or S. Examples are furyl, thienyl, pyrrolyl, oxinyl, dioxinyl or pyridyl. 5- or 6-membered rings are preferred.

As a heterocyclic radical R is for example pyrrolyl, pyrrolidinyl, oxazolyl, pyridinyl, 1,3-diazinyl, 1,2-diazinyl, piperidinyl, morpholinyl, thianthrenyl, furanyl, pyranyl, xanthenyl, imidazolyl, thiazoylyl, pyrimidinyl, indazolinyl, indolyl, indazolyl, purinyl, isoquinolyl, quinolyl, xanthyl, thioxanthyl, acridinyl etc.

Where OR$_8$, SR$_9$ or NR$_{10}$R$_{11}$-substituted naphthyl, anthracyl, phenanthryl or heterocyclic rings form 5- or 6-membered rings with the radicals R$_8$, R$_9$, R$_{10}$ and/or R$_{11}$, this embraces for example the following structures

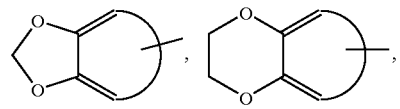

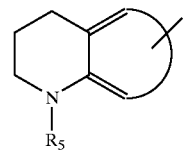

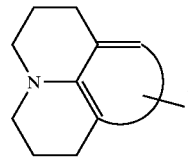

in which the arc and the two double bonds are the aromatic ring system in question.

Where R$_3$, R$_4$, R$_5$, R$_6$ or R$_7$ as OR$_8$, SR$_9$ or NR$_{10}$R$_{11}$ form a 5- or 6-membered ring with further substituents on the phenyl ring or with a carbon atom of the phenyl ring, this includes for example the following systems:

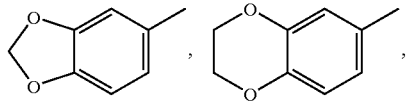

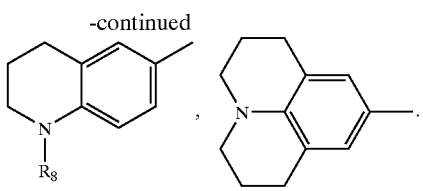

Where $R_{10}$ and $R_{11}$, together with the nitrogen atom to which they are attached, form a 5- or 6-membered ring which may also be interrupted by —O— or —$NR_{14}$—, the rings in question are, for example, saturated or unsaturated rings, examples being aziridine, piperazine, pyrrole, pyrrolidine, oxazole, pyridine, 1,3-diazine, 1,2-diazine, piperidine or morpholine; in particular, morpholinyl, piperidinyl or piperazinyl rings are formed.

The units of the formulae IIIa1, IIIa2, IIIb and/or IIIc are arranged randomly or in blocks; i.e. the sequence of these units in the depiction of the formula III is arbitrary. For example, blocks of units of the formula IIIa1, IIIa2, IIIb, IIIc may follow one another, but it is also possible for the individual units to be linked in a randomly distributed fashion, depending on the siloxane used for the preparation.

X, $X_1$ and $X_2$ as $C_1$–$C_{10}$alkylene are in each case linear or branched alkylene, examples being $C_1$–$C_8$-, $C_1$–$C_6$-, $C_1$–$C_4$-, $C_2$–$C_8$-, $C_2$–$C_4$alkylene, such as methylene, ethylene, propylene, isopropylene, n-butylene, sec-butylene, iso-butylene, tert-butylene, pentylene, hexylene, heptylene, octylene, nonylene or decylene. Branched alkylene is for example

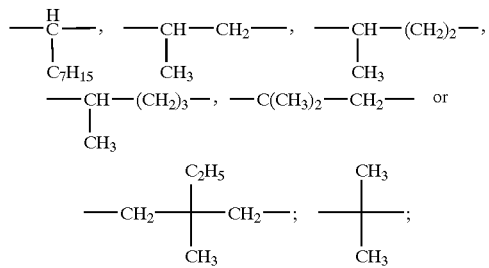

$Y_1$ as $C_1$–$C_{12}$alkylene may have the same definitions as indicated above and additionally may also, for example, be undecylene or dodecylene.

$Y_1$ as $C_4$–$C_{40}$alkylene interrupted one or more times by —O—, —S— or —$NR_{25}$— is linear or branched in the alkylene radical and is interrupted for example by 1–20, 1–12, 1–8 —O—, —S— and/or —$NR_{25}$—. This results in structural units, for example such as —$CH_2$—O—$CH_2$—, —$CH_2CH_2$—O—$CH_2CH_2$—, —[$CH_2CH_2$O]$_y$—, where y=1–20, —($CH_2CH_2$O)$_{18}CH_2CH_2$—, —$CH_2$—CH($CH_3$)—O—$CH_2$—CH($CH_3$)—, —$CH_2$—S—$CH_2$—, —$CH_2CH_2$—S—$CH_2CH_2$—, —$CH_2CH_2CH_2$—S—$CH_2CH_2CH_2$—, —($CH_2$)$_3$—S—($CH_2$)$_3$—S—($CH_2$)$_3$—, —$CH_2$—($NR_5$)—$CH_2$—, —$CH_2CH_2$—($NR_5$)—$CH_2CH_2$—.

$C_2$–$C_{10}$Alkenylene is mono- or polyunsaturated, linear or branched and is for example $C_2$–$C_8$-, $C_4$–$C_8$-, $C_3$–$C_6$-, $C_2$–$C_4$alkenylene, for example ethenylene, 1-propenylene, 1-butenylene, 3-butenylene, 2-butenylene, 1,3-pentadienylene, 5-hexenylene or 7-octenylene. $C_4$–$C_8$Alkenylene has the same definitions as indicated above, corresponding to the number of carbon atoms.

$C_2$–$C_{10}$Alkynylene is mono- or polyunsaturated, linear or branched and is for example $C_2$–$C_8$-, $C_3$–$C_6$-, $C_2$–$C_4$alkynylene. Examples are hexynylene, heptynylene, 2,4,4-trimethylpentynylene, 2-ethylhexynylene, octynylene, nonynylene or decynylene.

Y as the salt radical of the glyoxalic acid in question, together with the oxygen atom to which Y is attached, is for example —O⁻Y⁺. In this case Y is the cation of an alkali metal, particularly of Li, Na or K.

The term "from 200 nm into the IR region" denotes from 200 nm to 2500 nm, in particular from 200 nm to 1000 nm.

The term "and/or" is intended to denote that it is possible for not only one of the defined alternatives (substituents) to be present but also two or more different alternatives (substituents) of those defined together, i.e. mixes of different alternatives (substituents).

The term "at least" is intended to define one or more than one, for example one or two or three, preferably one or two.

Unless expressly described otherwise, in the description and the claims the word "comprising" is to be understood to include a defined subject or a defined group of subjects but without ruling out any other substances not mentioned exclusively.

"a", "b" and "c" are preferably a number from 0 to 10, especially 0–3;

"n" is preferably from 1 to 100; especially 1–20;

"p" is for example from 1 to 1000, from 1 to 100, from 1 to 50 or from 1 to 25; and "m" is from 0 to 100, for example from 0 to 50 or from 0 to 25, especially 0.

Where the siloxane starting material is a mixture of oligomeric siloxanes, "n" can also be less than 1 but greater than 0. In this case it is for example a number between 0.1 and 1000; 0.5 and 1000; 0.8 and 1000 etc.

A, $A_1$, $A_2$ and $A_3$ are preferably a radical of the formula III.

$R_1$ and $R_2$ are in particular a radical of the formula II or are naphthyl, preferably a radical of the formula II.

In the compounds of the formula Ia or Ib, if R, $R_1$ and/or $R_2$ are a radical of the formula II, at least one of the substituents $R_3$, $R_4$, $R_5$, $R_6$ or $R_7$ is a group —X-A, —$X_1$-$A_1$ or —$X_2$-$A_2$. For example, 1–3 or 1–2 or one of the substituents $R_3$, $R_4$, $R_5$, $R_6$ or $R_7$ is a group —X-A, —$X_1$-$A_1$ or —$X_2$-$A_2$. Preferably, 1 or 2 of the radicals $R_3$, $R_4$, $R_5$, $R_6$ or $R_7$ are —X-A, —$X_1$-$A_1$ or —$X_2$-$A_2$.

In particular, $R_3$, $R_7$ and/or $R_5$ are a group —X-A, —$X_1$-$A_1$ or —$X_2$-$A_2$. Preferably, $R_3$ and $R_5$ are a group —X-A, —$X_1$-$A_1$ or —$X_2$-$A_2$.

$R_3$, $R_4$, $R_5$, $R_6$ and $R_7$ are—besides a group —X-A, —$X_1$-$A_1$ or —$X_2$-$A_2$—particularly hydrogen, $C_1$–$C_4$alkyl or $C_1$–$C_4$alkoxy, preferably hydrogen.

$R_8$ and $R_9$ are in particular $C_1$–$C_4$alkyl, hydrogen, phenyl, —O-interrupted $C_2$–$C_8$alkyl, preferably $C_1$–$C_4$alkyl or hydrogen.

$R_{10}$ and $R_{11}$ are particularly $C_1$–$C_4$alkyl, preferably methyl, or together with the nitrogen atom to which they are attached form a morpholinyl radical.

$R_{12}$ is particularly $C_1$–$C_4$alkyl or phenyl.

$R_{14}$ is particularly hydrogen, $C_1$–$C_4$alkyl or OH-substituted $C_1$–$C_4$alkyl.

$R_{15}$, $R_{16}$ and $R_{17}$ are preferably $C_1$–$C_4$alkyl, especially methyl.

$R_{18}$ is particularly $C_1$–$C_4$alkyl, e.g. methyl.

$A_0$ is in particular a $C_6$–$C_{30}$alkyl radical, and is unsubstituted or substituted by halogen. Preference is given to $C_6$–$C_{18}$alkyl, unsubstituted or substituted by halogen, preferably fluorine. Where the radical $C_6$–$C_{30}$alkyl, is substituted by fluorine, it is preferably perfluorinated.

$A_4$ is in particular a $C_6$–$C_{30}$alkylene radical, and is unsubstituted or substituted by halogen. Preference is given to $C_6$–$C_{18}$alkylene, unsubstituted or substituted by halogen, preferably fluorine. Where the radical $C_6$–$C_{30}$alkylene is substituted by fluorine, it is preferably perfluorinated.

X, $X_1$ and $X_2$ are preferably $C_3$–$C_6$alkylene, —$(CH_2)_a$—O— or —$(CH_2)_a$—O—$(CH_2)_b$—O—, especially $C_3$–$C_6$alkylene or $(CH_2)_a$—O—$(CH_2)_b$—O—, a being particularly 2 and b being particularly 3.

Y is preferably $C_1$–$C_{24}$alkyl, especially methyl or ethyl.

Preparation Methods:

The compounds of the formula I are prepared by customary methods known to the person skilled in the art.

I. If A, $A_1$, $A_2$ or $A_3$ are a radical of the formula III, the compounds of the formula Ia and Ib may be obtained, for example, by reacting a photoinitiator with (at least one) alkenyl radical (XIV), (XIVa), (XIVb) aor (XIVc) and a siloxane (XV) in the presence of an appropriate catalyst:

in which IN, $IN_1$, $IN_2$, $IN_3$ are the radicals designated above, but where in the reaction the double bonds each become single bonds and the CH group becomes the $CH_2$ group. In other words, $CH_2$=CH— becomes —$CH_2$—$CH_2$— in the product, and $CH_2$=$CH_2$—$CH_2$— becomes —$(CH_2)_3$—;

R', $R'_1$, $R'_2$ are divalent radicals of the above-defined groups R, $R_1$ and $R_2$. If, for example, R is phenyl, then R' is phenylene.

$R_{15}$, $R_{16}$, $R_{17}$, $R_{18}$, X, $X_1$, $X_2$, Y, $Y_1$, $G_1$, $G_2$, n, m and p are as defined above.

Compounds of the formula Ic may be obtained under similar conditions with the proviso that in the reagent (XVa) $n \geq 2$.

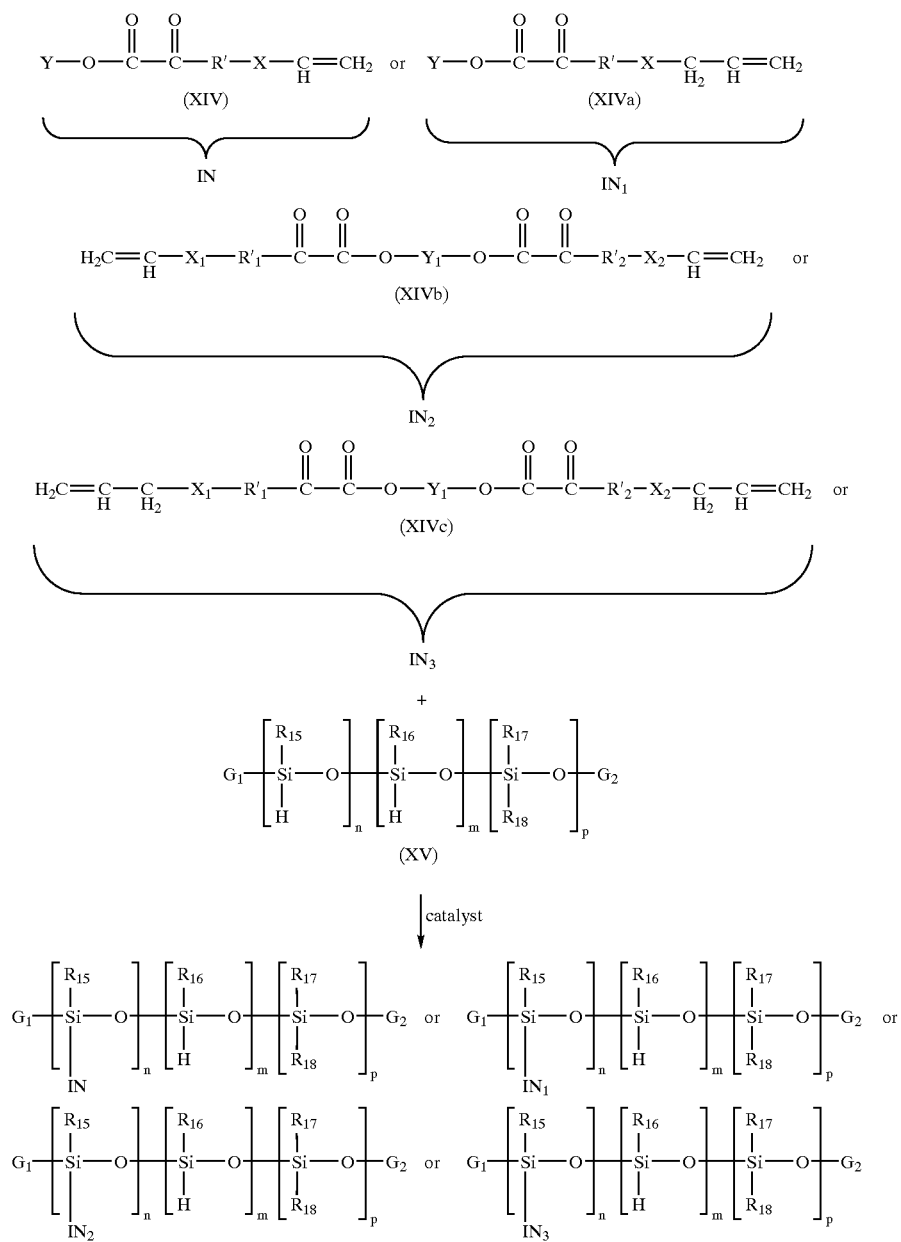

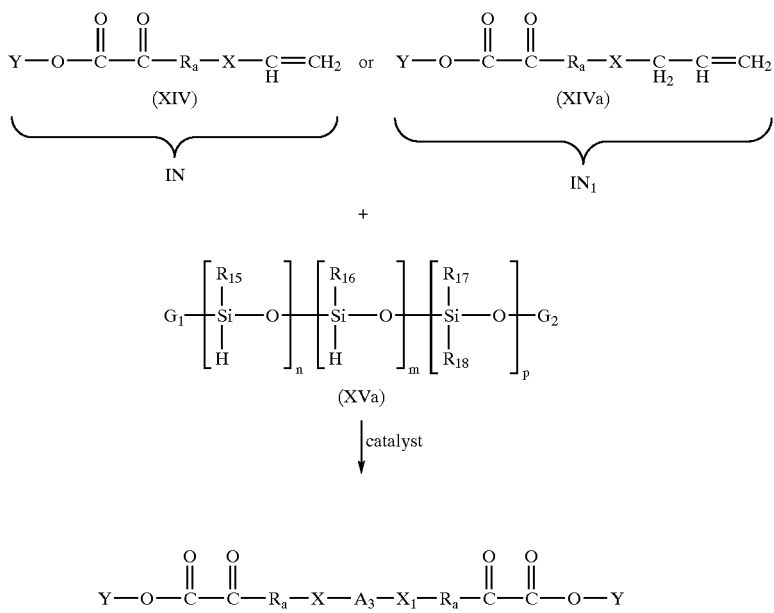

Compounds of the formula Ic may also be obtained, for example, starting from compounds of the formula (XIVb) or (XIVc) with (XVa).

Conditions for such reactions are known to the person skilled in the art. The molar ratios of the alkenyl-modified compounds (XIV), (XIVa), (XIVb) or (XIVc) and the siloxane compounds (XV) or (XVa) are guided in each case by the desired product and are generally not critical. For instance the amount of (XIV), (XIVa), (XIVb) or (XIVc) to be used is chosen according to the amount of free Si—H groups in (XV) or (XVa) and the respective desired degree of substitution of these groups. Where all the groups are to be consumed by reaction, it is appropriate, for example, to add (XIV), (XIVa), (XIVb) or (XIVc) in excess. It is, however, also possible to use an excess of component (XV) or (XVa).

The reaction temperatures are appropriately held within a range of 20–150° C., preferably 60–110° C. Moreover, it is appropriate to carry out the reaction, for example, in a suitable aprotic organic solvent, such as tetrahydrofuran (THF), dioxane, hexane, heptane, cyclohexane, toluene, xylene, benzene or chlorobenzene. It is also possible, however, to operate without solvents, for example.

The reaction mixture is normally stirred while the reaction is carried out.

It is also appropriate to carry out the reaction under inert conditions, four example under an argon or nitrogen atmosphere.

Examples of catalysts appropriate for carrying out the reaction are noble metal catalysts, such as platinum or rhodium catalysts. Examples are $H_2PtCl_6$ or $PtCl_2(C_6HF_5—CH=CH_2)_2$. These catalysts may also, for example, have been applied to suitable support materials, such as alumina, such as $Pt/Al_2O_3$ (for example, available from Heraeus). Carbon, for example, may also be used as a support material (Pt/C—which catalyst need not be anhydrous—available, for example, from Johnson Matthey). Examples of suitable catalysts are platinum, palladium, rhodium, nickel, cobalt or other metals, especially as powders or in the form of complexes. Examples are platinum sponge, platinum black, chloroplatinic acid, the reaction product of chloroplatinic acid and alcohol, and a complex of chloroplatinic acid and vinylsiloxane. Catalysts of this kind are available commercially, e.g. platinum-carbonyl-cyclovinylmethylsiloxane complex, platinum-diviniyltetramethyldisiloxane complex, platinum-octyl aldehyde/octanol complex, or may be obtained by methods customary in the art and known to the person skilled in the art.

The concentration of the catalyst is appropriately for example 1–1000 ppm, e.g. 150–400 ppm.

Such reactions are described, for example, in U.S. Pat. No. 4,507,187, EP-A 0 162 572 or in EP-A 0 088842.

II. Another way of preparing the surface-active photoinitiators is to react a photoinitiator containing a corresponding silyl group with an alkenyl-modified siloxane:

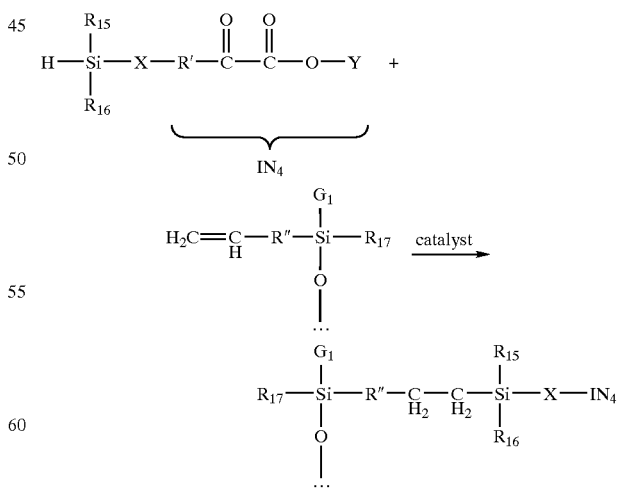

The reaction with the following starting material takes place in analogy to the equation given above, doubling the amount of siloxane starting material.

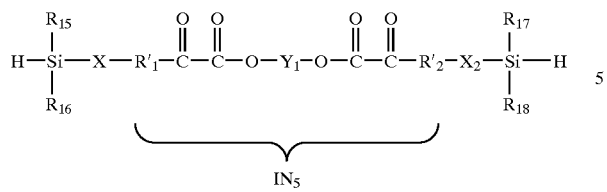

$X$, $X_1$, $R$, $R'_1$, $R'_2$, $R_{15}$, $R_{16}$, $R_{17}$, $R_{18}$ and $G_1$ have the definitions stated above; R" is an alkylene radical; " . . . " means that the radical of the siloxane molecule moiety defined in formula III adjoins this site (in accordance with formula III, in this reaction m must be 0 in the starting material).

The reaction conditions for this method correspond to those described above. In the literature such reactions are set out, for example, in U.S. Pat. No. 4,391,963 and JMS Pure Applied Chem. A31 (3) (1994), 305.

III. The surface-active photoinitiators may also be obtained, for example, by reacting an OH-containing initiator and a siloxane:

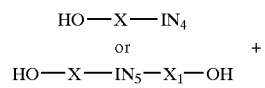

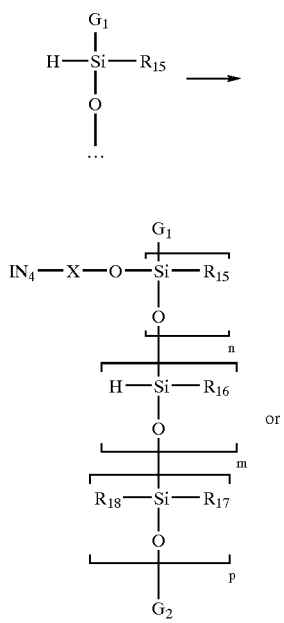

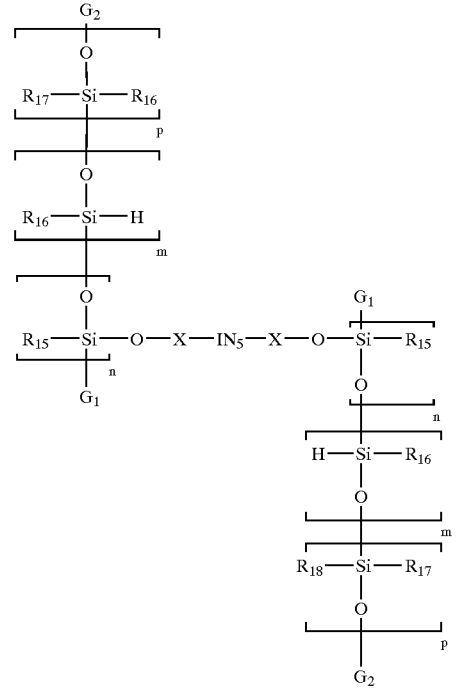

$IN_4$, $IN_5$, $X$, $X_1$, $R_{15}$, $R_{16}$, $R_{17}$, $G_1$, n, m, p, $R_{18}$ and $G_2$ have the definitions stated above; " . . . . " means that the radical of the siloxane molecule moiety defined in formula III adjoins this site. Suitable catalysts for this reaction are, for example, tin octoate, dibutyltin dilaurate, zinc octanoate, tin octanoate and zinc hexanoate. Examples of such reactions (albeit with the examples containing a sensitizer unit instead of the photoinitiator unit) can be taken from U.S. Pat. No. 4,921,589.

IV. L. Lecamp et al. in JMS Pure Appl. Chem. A 34(11) (1997), 2335–2353 describe a method of preparing siloxane-containing initiators in which an initiator comprising an $Si(OR)_{1-3}$ group and a siloxane having an $Si—(OH)_{1-2}$ group are reacted. Dibutyltin dilaurate, for example, is used as catalyst:

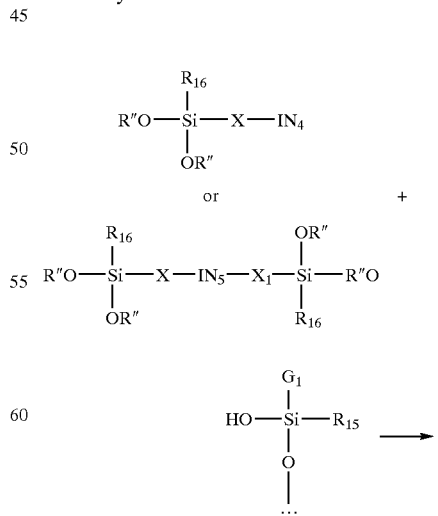

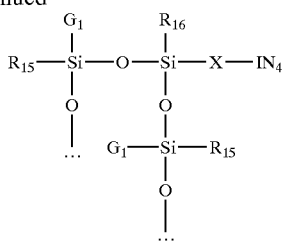

and also the corresponding dimeric molecule with $IN_5$.

$IN_4$, $IN_5$, X, $X_1$, $R_{15}$, $R_{16}$ and $G_1$ have the definition indicated above; R" is alkyl, especially methyl; "..." means that the radical of the siloxane molecule moiety defined in formula III adjoins this site.

V. Surface-active photoinitiators in accordance with the present invention may also be obtained, for example, by reacting a photoinitiator containing at least one carbonyl group on the aromatic ring with a siloxane containing a C—C double bond as end group (e.g. allyl or vinyl).

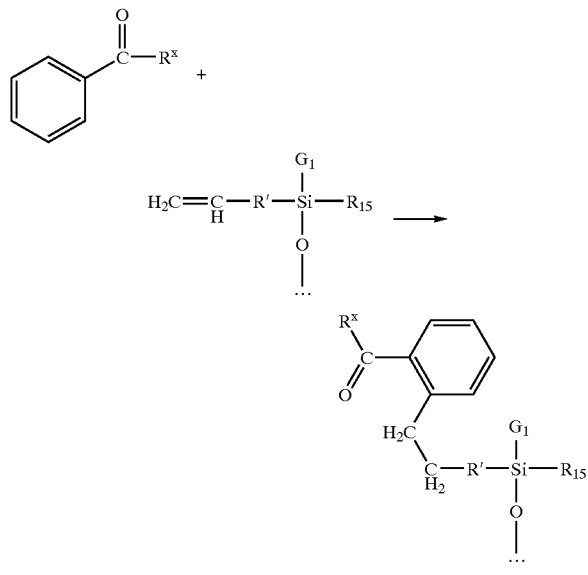

$R_{15}$ and $G_1$ have the definition indicated above; in the examples of the literature references cited later on below, $R^x$ together with the adjacent carbonyl group forms a benzoin, an α-hydroxy ketone or an α-amino ketone; R' is alkylene; "..." means that the radical of the siloxane molecule moiety defined in formula III adjoins this site. The application of this reaction to the preparation of glyoxalate esters of the present invention is novel. The reaction may be carried out on compounds of both the type $IN_7$ and the type $IN_8$.

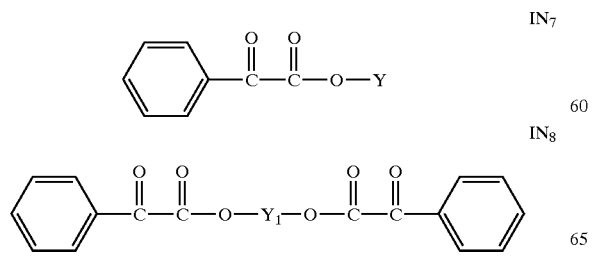

This reaction is published in U.S. Pat. No. 5,776,658. Examples of suitable catalysts for this reaction are ruthenium compounds as described by Murai et al. in Nature 366 (1993) 529.

VI. U.S. Pat. No. 4,477,326 and JP 9-328522-A describe the polymerization or copolymerization of polyalkoxysiloxanes in the presence of a base or of an acid catalyst. The method described is also suitable for preparing surface-active photoinitiators of the invention:

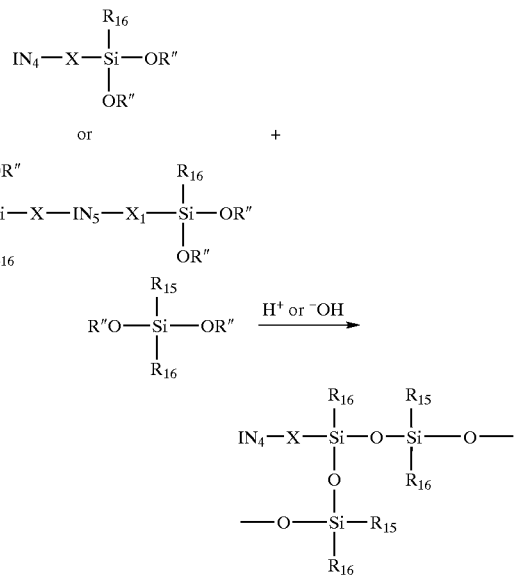

and also the corresponding dimeric molecule with $IN_5$.

$IN_4$, $IN_5$, X, $X_1$, $R_{15}$ and $R_{16}$ have the definition indicated above; R" is alkyl.

In this reaction, both polymeric and cyclic products may be obtained.

VII. Another method which can be used to prepare surface-active photoinitiators is set out, for example, in U.S. Pat. Nos. 4,587,276 and 4,477,276: the polymerization or copolymerization of siloxanes having hydrolysable groups (e.g. Si—Cl) in the presence of water:

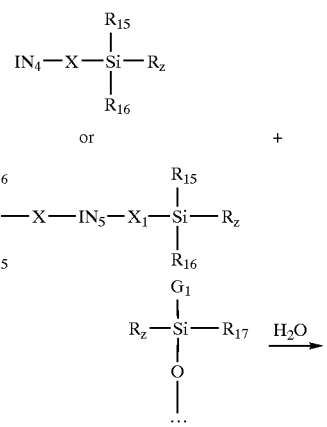

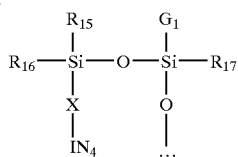

and also the corresponding dimeric molecule with $IN_5$.

$IN_4$, $IN_5$, X, $X_1$, $R_{15}$, $R_{16}$, $R_{17}$ and $G_1$ have the definition indicated above; $R_z$ is, for example, Cl or $OCH_3$; " . . . " means that the radical of the siloxane molecule moiety defined in formula III adjoins this site.

VIII. In J.M.S. Pure Appl. Chem. A 31(3) (1994), 305–318 A. Kolar et al. describe the preparation of photoinitiators with siloxane radicals starting from 1,4-dichlorobenzene. Grignard reaction is used to create a reactive centre which is reacted with dimethyldichlorosilane or dimethylmonochlorosilane to the corresponding silyl-modified chlorobenzene, onto which the corresponding α-cleavable photoinitiator carbonyl radical is introduced by means of further reactions. It is also possible similarly to obtain compounds of the formula (Ia) or (Ib) by introducing the corresponding photoinitiator-glyoxalic radical.

IX. L. Pouliquen et al. in Makromol. Chem. 193 (1992) 1273–1282 published a multistage reaction of photoinitiators containing acidic groups and a siloxane containing epoxide radicals in the presence of acetic anhydride (the photoinitiator compounds in this reference are of the phenone/tert-amine type). This process too may be used to prepare the compounds of the invention.

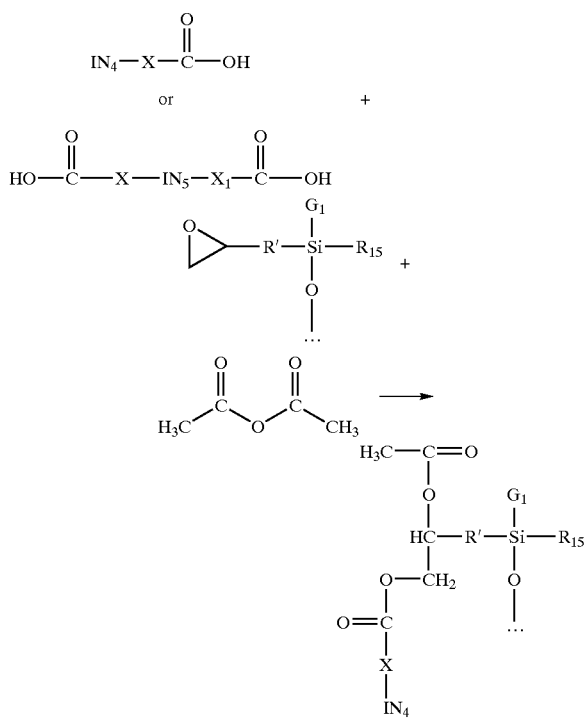

and also the corresponding dimeric molecule with $IN_5$.

$IN_4$, $IN_5$, X, $X_1$, $G_1$ and $R_{15}$ have the definition indicated above; R' is alkylene; " . . . " means that the radical of the siloxane molecule moiety defined in formula III adjoins this site.

X. Photoinitiators containing isocyanate groups and siloxanes containing hydroxyl or amine groups may likewise be reacted to give surface-active photoinitiators:

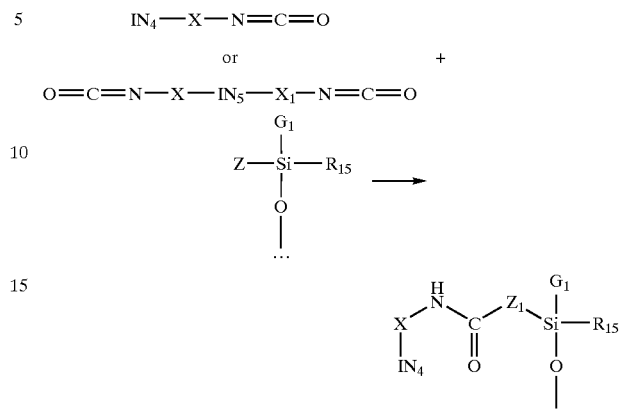

and also the corresponding dimeric molecule with $IN_5$.

$IN_4$, $IN_5$, X, $X_1$, $G_1$ and $R_{15}$ have the definitions indicated above; Z is $NH_2$ or OH; $Z_1$ is NH or O; " . . . " means that the radical of the siloxane molecule moiety defined in formula III adjoins this site.

Such reactions are described, for example, in WO 96/20919.

XI. Photoinitiators substituted by cyclic siloxane radicals may be obtained, for example, by carrying out the reactions described above with a cyclic siloxane, e.g. XI.

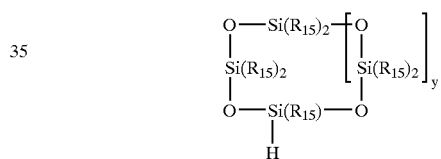

To prepare photoinitiators with cyclic siloxane radicals it is, however, also possible first to introduce linear siloxane radicals, by means for example of the methods described above, and then to cyclize these radicals by the action of a base, for example sodium hydroxide, or by the action of an acid.

The synthesis of surface-active photoinitiators containing cyclic siloxane radicals may take place, for example, as described above by reacting a cyclic siloxane with the respective initiator moiety:

IN; $IN_1$, $IN_2$, $IN_3$ (XIV, XIVa, XIVb or XIVc) +

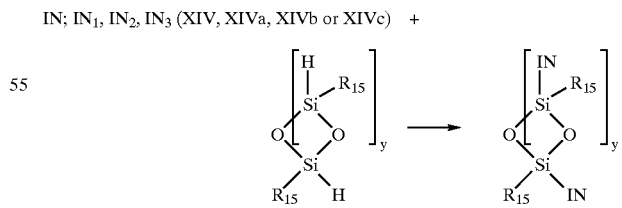

(IN, $IN_1$, $IN_2$, $IN_3$ and $R_{15}$ are as defined above; y defines the ring size; in the above formula IN only is given, as representative of IN, $IN_1$, $IN_2$ and $IN_3$).

Also possible is a cyclization reaction of a siloxane-modified initiator moiety containing OR groups in the presence of acid or alkali:

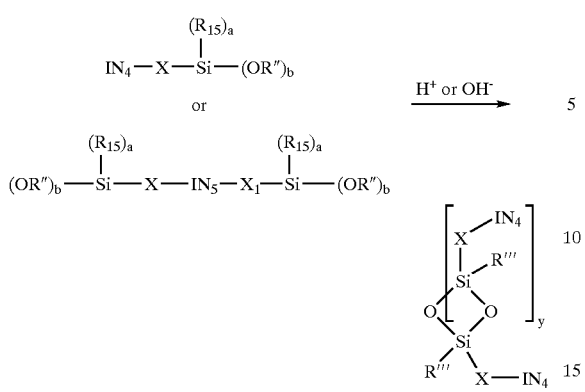

and also the corresponding molecule with $IN_5$.

$IN_4$, $IN_5$, X, $X_1$ and $R_{15}$ are as defined above; R" is alkyl; a=0 or 1; b=2 or 3, the sum a+b=3; depending on the definition of a and b, R'" is either $R_{15}$ or OR".

Furthermore, cyclic compounds may be formed by reacting a siloxane-modified initiator moiety containing OR groups with a siloxane containing OR" groups:

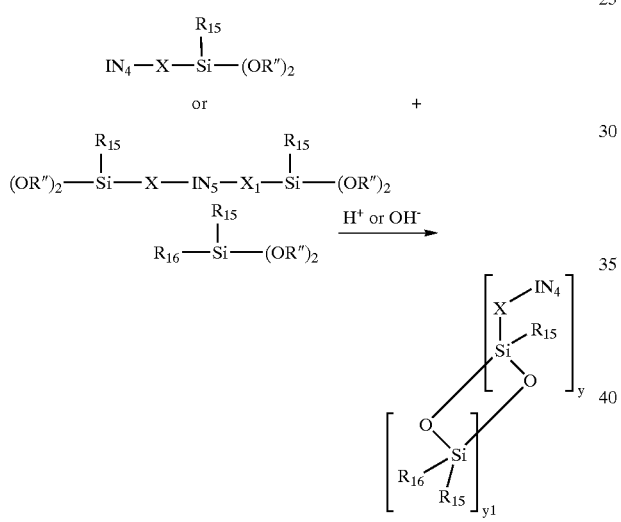

and also the corresponding molecule which is dimeric by way of $IN_5$.

($IN_4$, $IN_5$, X, $X_1$, $R_{15}$ and $R_{16}$ are as defined above; R" is alkyl; the sum of y and y1 defines the number of ring members)

The distribution of the $Si(IN_4)(R_{15})$, $Si(IN_5)(R_{15})$ and $Si(R_{15})(R_{16})$ groups in this case is random or blockwise.

In order to obtain compounds of the formula Ic, in each case use is made of siloxane reagents having the corresponding number of functional (i.e. reactive) groups (especially having 2 functional groups) in the reactions I.–XI.

In the preparation of the siloxane-containing photoinitiators it is also possible for mixtures of active compounds to be formed. These mixtures may be separated in accordance with customary methods, such as distillation, crystallization or chromatography, or else may be used as they are as surface-active photoinitiators in compositions which are to be polymerized.

XII. Compounds of the formula Ia and Ib in which A, $A_1$ or $A_2$ are $A_0$ may be obtained, for example, by Friedel-Crafts alkylation of a photoinitiator (XVI) or (XVIa) with a corresponding alkyl halide (XVII) in the presence of an appropriate catalyst:

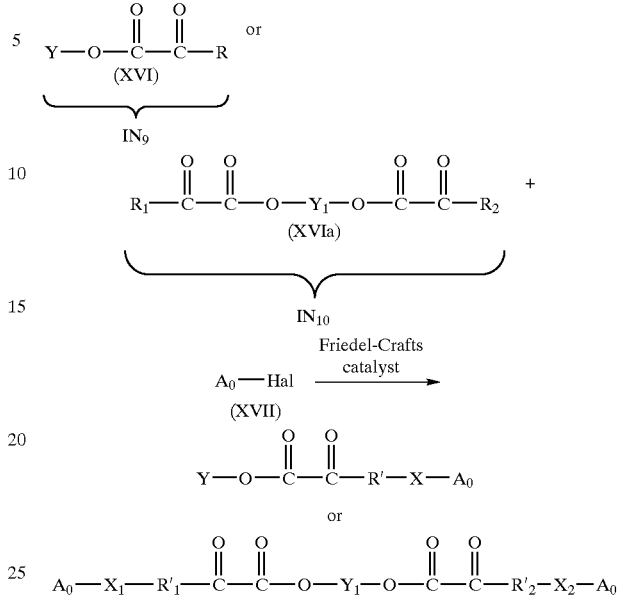

in which R, R', $R_1$, $R'_1$, $R_2$, $R'_2$, Y, $Y_1$ and $A_0$ are as defined above;

X, $X_1$ and $X_2$ are single bonds.

The conduct of such reactions is known to the person skilled in the art and is described at length in the literature (e.g. J. March, Advanced Organic Chemistry, $3^{rd}$ ed. 1985, section 1–13, pages 479–484; or Olah, "Friedel-Crafts Chemistry", Wiley NY 1973; and also Roberts and Khalaf, "Friedel-Crafts Alkylation Chemistry", Marcel Dekker NY 1984).

Such compounds are also described in JCS Perkin I (1996) 1141.

Compounds of the formula Ia in which A is $A_0$ may be prepared by Friedel-Crafts acylation of aralkyl compounds containing the radical $A_0$ with oxalic acid chloride monoalkyl ester in the presence of an appropriate catalyst

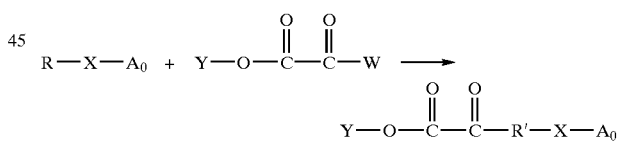

in which R, R', X and $A_0$ are as defined above and W is —OH or halogen, preferably —Cl.

Compounds of the formula Ic in which $A_3$ is $A_4$ may be obtained correspondingly by Friedel-Crafts acylation of aralkyl with oxalyl dichloride. The conduct of these reactions is known to the person skilled in the art and is described at length in the literature (e.g. J. March, Advanced Organic Chemistry, $3^{rd}$ ed. 1985, section 1–13, pages 479–484; or Olah, "Friedel-Crafts Chemistry", Wiley NY 1973); such compounds are also described by Kuzmenko et al. in JCS (1999) 121 (12) 2657.

XII. Compounds of the formula Ia and Ib may also be obtained by the customary reactions, known to persons skilled in the art, of etherification or alkylation of a thiol group or of an amine group. For example, compounds of the formula Ia and Ib may be prepared by reacting a photoinitiator (XVIII) or (XVIIa) with an alkyl halide (XVII) in the presence of a base:

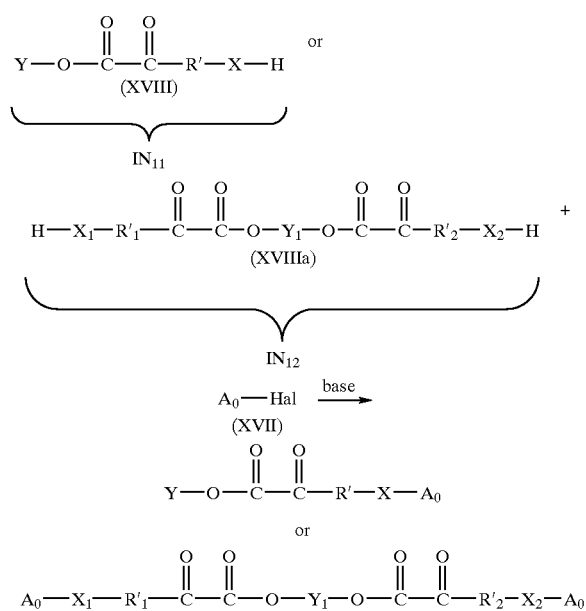

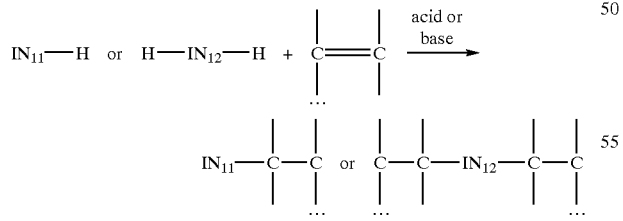

in which R', $R'_1$, $R'_2$, Y, $Y_1$ and $A_0$ are as defined above; X, $X_1$ and $X_2$ are —O—, —S— or —$NR_{14}$— groups.

Such reactions are known to the person skilled in the art and are described at length in the literature (e.g. J. March in Advanced Organic Chemistry, $3^{rd}$ ed. 1985). If X, for example, is —O—, this reaction corresponds to a Williamson ether synthesis (J. March in Advanced Organic Chemistry, $3^{rd}$ ed. 1985, section 0–14, page 342–343); if X is —S—, the reaction is described, for example, by J. March in Advanced Organic Chemistry, $3^{rd}$ ed. 1985, section 3–5, page 589–590; if X is —$NR_{14}$—, the reaction corresponds to the alkylation of an amine (J. March in Advanced Organic Chemistry, $3^{rd}$ ed. 1985, section 0–45, page 364–366).

XIV. Compounds of the formula Ia and Ib may also be obtained by acid- or base-catalysed addition reaction of alcohols (J. March in Advanced Organic Chemistry, $3^{rd}$ ed. 1985, section 5–4, page 684–685) or of mercaptans (J. March in Advanced Organic Chemistry, $3^{rd}$ ed. 1985, section 5–6, page 687–688) with olefins. In this reaction the olefinic bond may be present both on the R, $R_1$ or $R_2$ group of the photoinitiator and also in the surface-active group that is to be inserted ($A_4$, $A_0$), and accordingly the hydroxyl or thiol group may be both in the surface-active group and in the R, $R_1$ or $R_2$ group of the photoinitiator. For example:

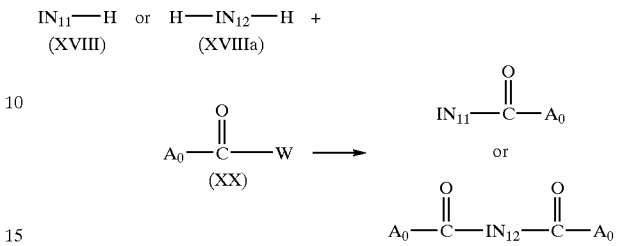

in which $IN_{11}$ and $IN_{12}$ are as defined above; X, $X_1$ and $X_2$ in this case are —O— or —S— groups; " . . . " means that the radical of $A_0$ or $A_4$ adjoins this site.

XV. Compounds of the formula Ia and Ib may also be obtained by acylation of corresponding photoinitiators in which X is an —O—, —S— or —$NR_{14}$— group. The various possible conditions for such reactions are known to the person skilled In the art. For example, a compound Ia or Ib may be reacted by acylating a photoinitiator (XVIII) with a corresponding surface-active reagent (XX) containing an acid group or an acid chloride group to give an ester, a thiol ester or an amide. Similar reactions may also be made starting from the photoinitiator (XVIIIa).

$IN_{11}$—H   or   H—$IN_{12}$—H   +
(XVIII)              (XVIIIa)

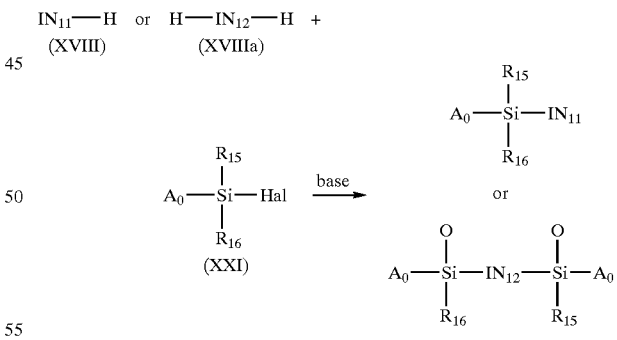

in which $IN_{11}$, $IN_{12}$ and $A_0$ are as defined above; X in this case is —O—, —S— or —$NR_{14}$—; W is —OH or -Hal, where -Hal is particularly —Cl.

These reactions are known to the person skilled in the art and are described at length in the customary textbooks of organic chemistry, e.g. in J. March, Advanced Organic Chemistry, $3^{rd}$ ed. 1985.

XVI. Compounds of the formula Ia and Ib may also be prepared by silylation of corresponding photoinitiators in which X is an —O—, —S— or —$NR_{14}$— group. The various possible conditions for such reactions are known to the person skilled in the art. For example, the compound Ia may be prepared by silylation of a photoinitiator (XVIII) with a corresponding surface-active reagent (XXI) which carries a silyl-active group, such as a group

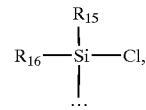

for example. Similar reactions may also be produced starting from the photoinitiator (XVIIIa). Where the surface-active reagent contains more than one reactive silyl group, compounds of the formula Ic are obtained.

$IN_{11}$—H   or   H—$IN_{12}$—H   +
(XVIII)              (XVIIIa)

in which $IN_{11}$, $IN_{12}$, $R_{15}$, $R_{16}$ and $A_0$ areas defined above; X in this case is —O—, —S— or —$NR_{14}$—; -Hal is a halogen atom, especially Cl.

Such reactions are described, for example, by Lalonde and Chan in Synthesis (1985), (9), 817–45.

The products of the formula Ia obtained by the above-described reactions I.–XVI may, for example, be subsequently transesterified. In this case it is possible, for example, to replace the radical Y by a group $Y_1$.

In analogy to the above-described reactions XII.–XVI. it is of course also possible to prepare compounds of the formula Ic in which $A_3$ is a surface-active radical $A_4$, using the corresponding starting materials.

The alkenyl-modified photoinitiators (XIV) and (XIVa) may be prepared by methods known to the person skilled in the art, for example by the method described in U.S. Pat. No. 4,507,187 or in EP 161830. Appropriate methods are also published in WO 98/33761.

Some of the siloxane compounds (V) are available commercially, or they may be obtained by methods known to the person skilled in the art. For example, methods of preparation and/or literature citations for the preparation can be found in the Geleste catalogue "ABCR Geleste 2000", pages 434–447.

In the preparation of asymmetric compounds of the formula Ib or Ic, i.e. those in which $R_1$ and $R_2$ and/or $R_a$ and $R_b$ are not identical, the reaction is carried out using the corresponding different starting materials, appropriately in a ratio of 1:1.

Where alcohol is liberated in one of the above-described reactions, it is appropriate to ensure that the alcohol which forms during the reaction isremoved from the reaction mixture. This is done, for example, by means of distillation.

Depending on the solvents and starting materials used the reactions are conducted at different temperatures. The temperatures and other reaction conditions required for the corresponding reactions are common knowledge and are well known to the person skilled in the art. The reaction products may be separated and purified by customary methods, such as by crystallization, distillation or chromatography.

The preparation of the photoinitiator starting materials which in accordance with the invention are surface-actively modified with A or $A_3$ is known to the person skilled in the art and is performed in accordance with customary methods. The preparation of the glyoxalic ester initiators, for example, is described in U.S. Pat. Nos. 4,475,999, 4,038,164, EP 132868, GB 1534320, U.S. Pat. Nos. 4,279,718, 4,308,394, 3,930,868 and WO 98/33761.

Preference is given to compounds of the formula Ia, Ib and Ic wherein

R, $R_1$ and $R_2$ independently of one another are a radical of the formula II indicated above, or R, $R_1$ and $R_2$ are naphthyl, the naphthyl radical being unsubstituted or substituted by A-X—, $A_1$-$X_1$—, $A_2$-$X_2$—, $C_1$–$C_8$-alkyl, phenyl or $OR_8$, with the proviso that there is at least one substituent A-X—, $A_1$-$X_1$— or $A_2$-$X_2$— in the radical R or in at least one of the radicals $R_1$ or $R_2$;

$R_3$, $R_4$, $R_5$, $R_6$ and $R_7$ independently of one another are hydrogen; A-X—, $A_1$-$X_1$—, $A_2$-$X_2$—;

unsubstituted $C_1$–$C_{12}$alkyl; or $C_2$–$C_{12}$alkyl which is interrupted by one or more non-successive oxygen atoms; or $R_3$, $R_4$, $R_5$, $R_6$ and $R_7$ are halogen, $OR_8$ or unsubstituted phenyl, with the proviso that at least one radical $R_3$, $R_4$, $R_5$, $R_6$ or $R_7$ is A-X—, $A_1$-$X_1$— or $A_2$-$X_2$—;

$R_8$ is hydrogen or unsubstituted $C_1$–$C_{12}$alkyl; or is $C_2$–$C_{12}$alkyl which is interrupted by one or more non-successive oxygen atoms; or is phenyl, $C_3$–$C_6$alkenyl, cyclopentyl or cyclohexyl, these radicals being unsubstituted;

$R_a$ and $R_b$ independently of one another are phenylene or naphthylene, these radicals being unsubstituted or substituted by A-X—, $A_1$-$X_1$—, $A_2$-$X_2$—, $C_1$–$C_8$-alkyl, phenyl or $OR_8$, A, $A_1$ and $A_2$ independently of one another are a surface-active radical of the formula III indicated above; or A, $A_1$ and $A_2$ are a surface-active radical $A_0$; where $A_0$ is $C_6$–$C_{30}$alkyl, $C_6$–$C_{30}$aralkyl, $C_6$–$C_{30}$alkyl-(CO)—, $C_6$–$C_{30}$aralkyl-(CO)—, $C_6$–$C_{30}$alkyl-Si($R_{15}$)($R_{16}$)—, these radicals being unsubstituted or substituted by F;

n is defined as indicated above;

m is defined as indicated above;

p is defined as indicated above;

$A_3$ is a radical of the formula III in which n has a value from 2 to 100; or $A_3$ is a surface-active radical $A_4$; where $A_4$ is $C_6$–$C_{30}$alkylene, $C_6$–$C_{30}$aralkylene, $C_6$–$C_{30}$alkylene-(CO)—, $C_6$–$C_{30}$aralkylene-(CO)—, —(CO)—$C_6$–$C_{30}$alkylene-(CO)—, —(CO)—$C_6$–$C_{30}$aralkylene-(CO)—, $C_6$–$C_{30}$-alkylene-Si($R_{15}$)($R_{16}$)—, —Si($R_{15}$)($R_{16}$)—$C_6$–$C_{30}$-alkylene-Si($R_{15}$)($R_{16}$)—, these radicals being unsubstituted or substituted by F;

$G_1$ is defined as indicated above;

$G_2$ is defined as indicated above;

$R_{15}$, $R_{16}$, $R_{17}$, $R_{19}$, $R_{20}$, $R_{21}$, $R_{22}$, $R_{23}$ and $R_{24}$ independently of one another are $C_1$–$C_{18}$alkyl or phenyl;

$R_{18}$ is unsubstituted $C_1$–$C_{18}$alkyl or phenyl;

X, $X_1$ and $X_2$, if A, $A_1$, $A_2$ and $A_3$ are a radical of the formula III, are independently of one another $C_1$–$C_{10}$alkylene, —(CH$_2$)$_a$—O—, —O—(CH$_2$)$_a$—, —O—(CH$_2$)$_a$—O—, —(CH$_2$)$_a$—O—(CH$_2$)$_b$—, (CH$_2$)$_a$—O—(CH$_2$)$_b$—O—, —(CH$_2$)$_a$—NR$_{14}$—(CH$_2$)$_b$—, —(CH$_2$)$_a$—NR$_{14}$—, —(CH$_2$)$_a$—O—(CH$_2$)$_b$—NR$_{14}$—(CH$_2$)$_c$—, —(CH$_2$)$_a$—O—(CH$_2$)$_b$—NR$_{14}$—; and X, $X_1$ and $X_2$, if A, $A_1$ or $A_2$ have the definition of $A_0$ or $A_3$ has the definition of $A_4$, are independently of one another a single bond, —O—, —S— or —NR$_{14}$—;

$R_{14}$ is defined as indicated above;

a, b and c independently of one another are a number from 0 to 3; with the proviso that they are, however, at least 1 if the methylene group in question is between two oxygen atoms or one oxygen atom and one nitrogen atom;

Y is $C_1$–$C_{20}$alkyl which is unsubstituted or substituted by a group A-X—; or Y is phenyl or naphthyl; these radicals being unsubstituted or substituted by one or more groups A-X— and/or $C_1$–$C_{12}$alkyl; or Y is $C_1$–$C_4$alkyl which is substituted by phenyl, naphthyl, anthracyl, phenanthryl and, if desired, additionally by a group A-X—;

$Y_1$ is $C_1$–$C_{12}$alkylene which is unsubstiued or substituted by a group $A_1$-$X_1$—; cyclohexylene which is unsubstituted or substituted by a group $A_1$-$X_1$—, $C_4$–$C_{40}$alkylene which is interrupted one or more times by —O—, —S— or —NR$_{25}$— and which is unsubstituted or substituted by a group $A_1$-$X_1$—, or $Y_1$ is phenylene which is unsubstituted or substituted by a group $A_1$-$X_1$—; or $Y_1$ is a radical of the formulae V, VI, VII, VIII, IX, X, XI, XII, XIII, XIV or XV indicated above, the radicals of the formula V, VI, VII, VIII, IX, X, XI, XII, XIII, XIV or XV being unsubstituted or substituted by a group $A_1$-$X_1$—;

$Y_2$ is $Y_1$ with the exception of the formula VII;

$R_{25}$ has the definition indicated above.

Particular preference is given to compounds of the formula Ia, Ib and Ic wherein R, $R_1$ and $R_2$ independently of one another are a radical of the formula II indicated above, $R_3$, $R_4$, $R_5$, $R_6$ and $R_7$ independently of one another are hydrogen or A-X—, $A_1$-$X_1$—, $A_2$-$X_2$—;

with the proviso that at least one radical $R_3$, $R_4$, $R_5$, $R_6$ or $R_7$ is A-X—, $A_1$-$X_1$— or $A_2$-$X_2$—;

$R_a$ and $R_b$ are phenylene,

A, $A_1$ and $A_2$ independently of one another are a surface-active radical of the formula III indicated above; or A, $A_1$ and $A_2$ are a surface-active radical $A_0$, where $A_0$ is $C_6$–$C_{30}$alkyl or $C_6$–$C_{30}$alkyl-(CO)—, these radicals being unsubstituted or substituted by F;

n is an integer 1–100;

m is an integer 0–100;

p is an integer 1–100;

$A_3$ is a radical of the formula III in which n has a value from 2 to 100; or $A_3$ is a surface-active radical $A_4$, where $A_4$ is $C_6$–$C_{30}$alkylene or —(CO)—$C_6$–$C_{30}$alkylene-(CO)—, these radicals being unsubstituted or substituted by F;

$G_1$ is methyl or —O—Si($R_{19}$, $R_{20}$, $R_{21}$), $G_2$ is methyl or —Si($R_{22}$, $R_{23}$, $R_{24}$), with the proviso that, if $G_2$ is methyl, the radical $G_2$ is attached directly to the silicon atom without an oxygen bridge;

$R_{15}$, $R_{16}$, $R_{17}$, $R_{18}$, $R_{19}$, $R_{20}$, $R_{21}$, $R_{22}$, $R_{23}$ and $R_{24}$ independently of one another are methyl or phenyl;

X, $X_1$ and $X_2$, if A, $A_1$, $A_2$ and $A_3$ are a radical of the formula III, are independently of one another $C_1$–$C_{10}$alkylene, or —(CH$_2$)$_a$—O—; and X, $X_1$ and $X_2$, if A, $A_1$ or $A_2$ have the definition of $A_0$ or $A_3$ has the definition of $A_4$, are independently of one another a single bond or —O—;

a is a number from 1 to 3;

Y is unsubstituted $C_1$–$C_{20}$alkyl;

$Y_1$ is unsubstituted $C_1$–$C_{12}$alkylene interrupted one or more times by —O—;

or $Y_1$ is unsubstituted phenylene;

or $Y_1$ is a radical of the formulae V, VI, VII, VIII, IX, X, XI, XII, XIII, XIV or XV indicated above;

$Y_2$ is $Y_1$ with the exception of the formula VII;

$R_{25}$ has the definition indicated above.

By way of example, the following compounds are given:

I. Compounds of the formula Ia wherein

Y is unsubstituted alkyl;

R is a radical of the formula II where $R_3$ or $R_5$=AX;

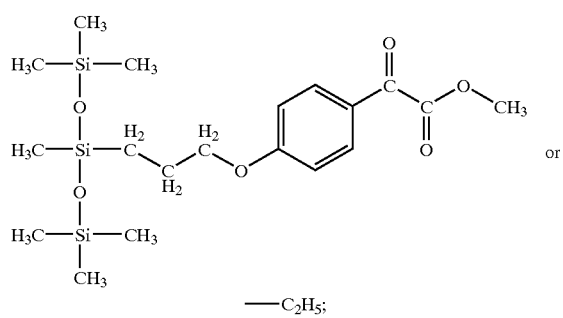

—$C_2H_5$;

A=radical of the formula III where n=1, m=0, p=0; $G_1$=—O—Si($R_{19}R_{20}R_{21}$), $G_2$=—Si($R_{22}R_{23}R_{24}$), X=—(CH$_2$)$_a$—O— where a=3, or —$C_2H_5$, A=radical of the formula III where n=1, m=0, p=0; $G_1$=—O—Si($R_{19}R_{20}R_{21}$), $G_2$=—Si($R_{22}R_{23}R_{24}$), X=—(CH$_2$)$_a$—O— where a=3 or —$C_2H_5$,

A=radical of the formula III where n=1, m=0, p=1, $G_1$=methyl, $G_2$=—Si($R_{22}R_{23}R_{24}$), X=—(CH$_2$)$_a$—O— where a=3 or —$C_2H_5$,

A=radical of the formula III where n=1, m=0, p=1, $G_1$=alkyl, $G_2$=—Si($R_{22}R_{23}R_{24}$), X=—(CH$_2$)$_a$—O— where a=3

—CH$_3$ or —$C_2H_5$

A=$A_0$ where $A_0$=$C_{18}H_{37}$, X=—O—;

—CH$_3$ or —$C_2H_5$

A=$A_0$ where $A_0$=fluorine-substituted alkyl-C(O).

II. Compounds of the formula Ib wherein $Y_1$ is unsubstituted alkylene, alkylene which is interrupted once by —O—, phenylene or a radical of the formula (XIII);

$R_1$ and $R_2$ are a radical of the formula II where $R_3$ or $R_5$=AX:

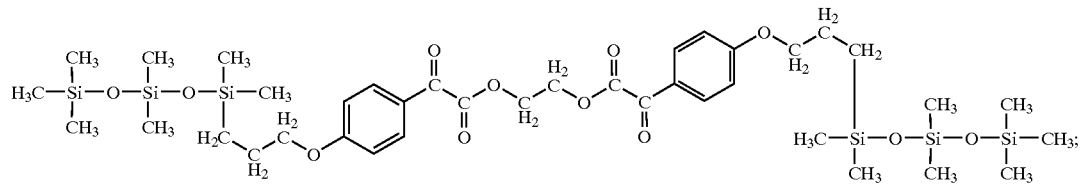

A=a radical of the formula III where n=1, m=0, p=1,
$G_1$=methyl, $G_2$=—Si($R_{22}R_{23}R_{24}$),
X=—(CH$_2$)$_a$—O—; a=3; $Y_1$=—C$_2$H$_4$—

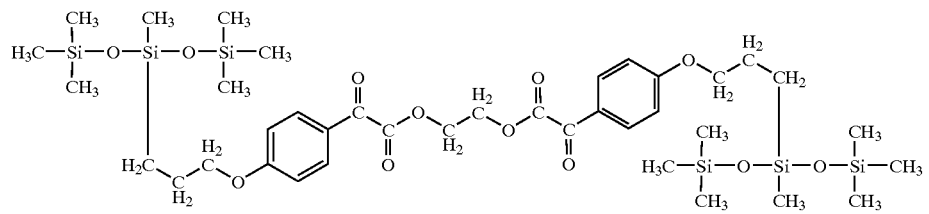

A=a radical of the formula III where n=1, m=0, p=0;
$G_1$=—O—Si($R_{19}R_{20}R_{21}$), $G_2$=—Si($R_{22}R_{23}R_{24}$),
X=—(CH$_2$)$_a$—O—; a=3; $Y_1$=—C$_2$H$_4$—

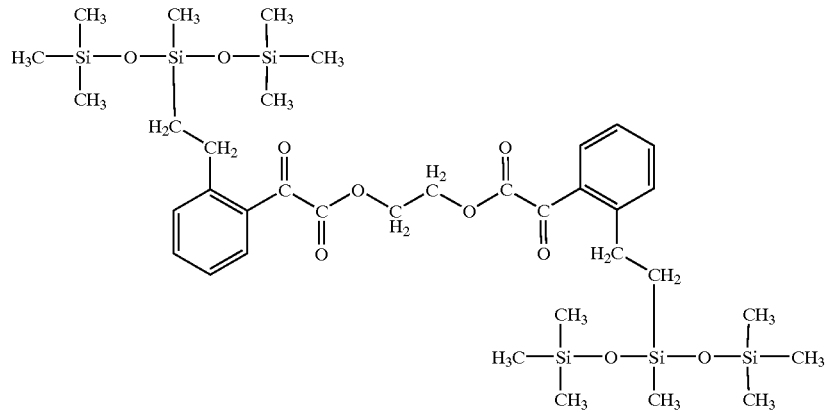

A=a radical of the formula III where n=1, m=0, p=0,
$G_1$=—O—Si($R_{19}R_{20}R_{21}$), $G_2$=—Si($R_{22}R_{23}R_{24}$),
X=—C$_2$H$_4$—; $Y_1$=—C$_2$H$_4$—

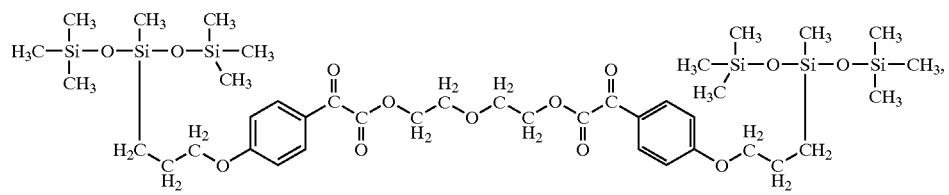

A=a radical of the formula III where n=1, m=0, p=0;
  $G_1$=—O—Si($R_{19}R_{20}R_{21}$), $G_2$=—Si($R_{22}R_{23}R_{24}$),
X=—(CH$_2$)$_a$—O—; a=3, $Y_1$=—C$_2$H$_4$—O—C$_2$H$_4$—

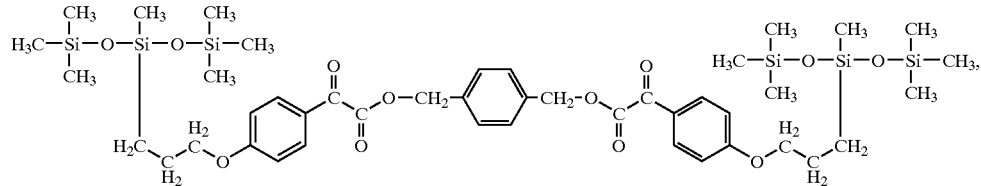

A=a radical of the formula III where n=1, m=0, p=0;
  $G_1$=—O—Si($R_{19}R_{20}R_{21}$), $G_2$=—Si($R_{22}R_{23}R_{24}$),
X=—(CH$_2$)$_a$—O—; a=3, $Y_1$=a radical of the formula XIII,

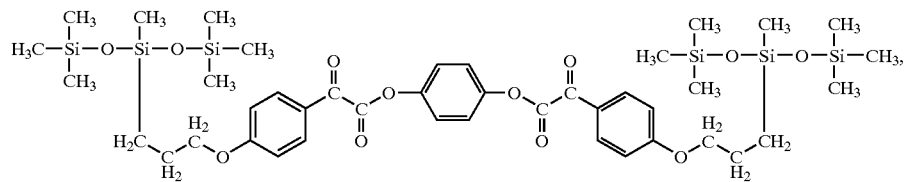

A=a radical of the formula III where n=1, m=0, p=0;
  $G_1$=—O—Si($R_{19}R_{20}R_{21}$), $G_2$=—Si($R_{22}R_{23}R_{24}$),
X=—(CH$_2$)$_a$—O—; a=3, $Y_1$=phenylene,

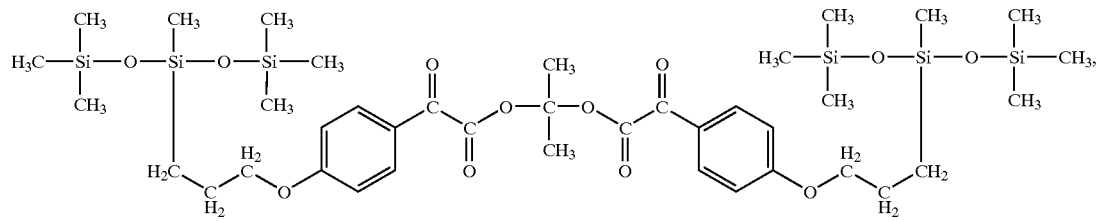

A=a radical of the formula III where n=1, m=0, p=0;
  $G_1$=—O—Si($R_{19}R_{20}R_{21}$), $G_2$=—Si($R_{22}R_{23}R_{24}$),
X=—(CH$_2$)$_a$—O—; a=3, $Y_1$=isopropylene,

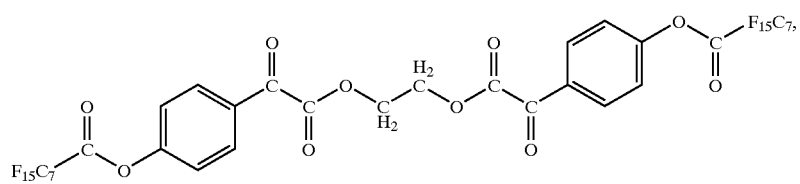

A=A$_0$, A$_0$=fluorine-substituted alkyl-C(O)
X=—O—; $Y_1$=—C$_2$H$_4$—.

III. Compounds of the formula Ic wherein

Y is unsubstituted alkyl;
R$_a$ and R$_b$ are phenylene;
X and X$_1$ are —(CH$_2$)$_a$—O—; a=3, or are ethylene:

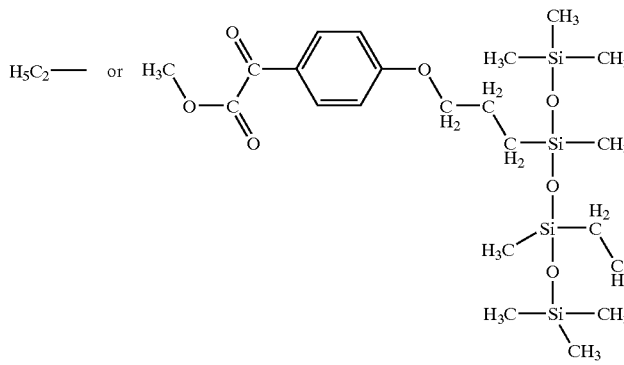

$A_3$=a radical of the formula III where n=2, m=0, p=0,
  $G_1$=—O—Si($R_{19}R_{20}R_{21}$), $G_2$=—Si($R_{22}R_{23}R_{24}$),
  X=$X_1$=—CH$_2$—CH$_2$—CH$_2$—O—

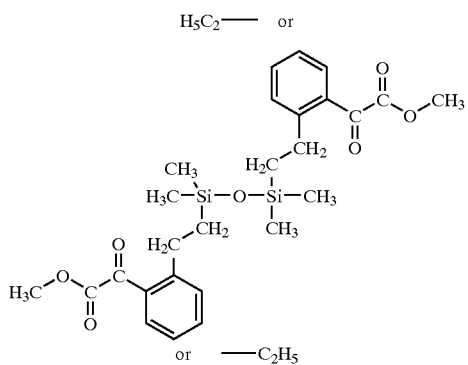

$A_3$=a radical of the formula III where n=2, m=0, p=0,
  $G_1$=methyl, $G_2$=methyl
  X=$X_1$=—CH$_2$—CH$_2$—

-continued

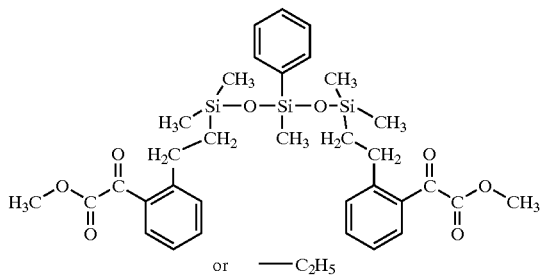

$A_3$=a radical of the formula III where n=2, m=0, p=1,
  $R_{17}$=phenyl, $G_1$=methyl, $G_2$=methyl;
  X=$X_1$=—CH$_2$—CH$_2$—,

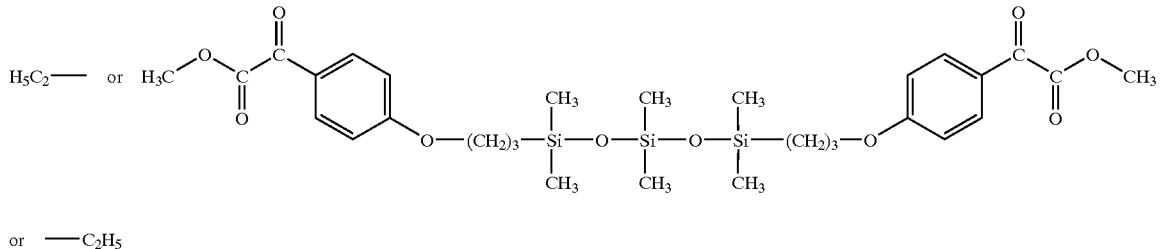

$A_3$=a radical of the formula III where n=2, m=0, p=1,
  $G_1$=methyl, $G_2$=methyl;

X=$X_1$=—CH$_2$—CH$_2$—CH$_2$—O—,

-continued

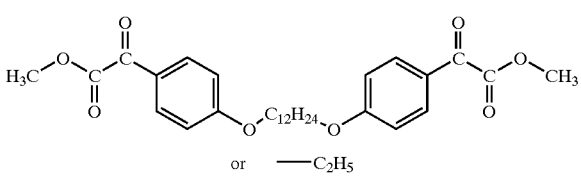

$A_3=A_4$, $A_4$=—$CH_{12}H_{24}$—, X and $X_1$ are —O—,

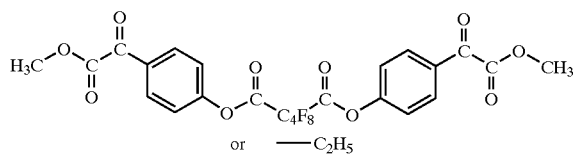

$A_3=A_4$, $A_4$=fluorine-substituted (O)C-alkylene-C(O), X and $X_1$ are —O—.

In the compounds of the formula I there is at least one substituent —X-A-, $X_1$-$A_1$ or —$X_2$-$A_2$ on the aryl ring of the compound, i.e. on the phenyl radical (of the formula II), the naphthyl, anthracyl, phenanthryl or heterocyclic radical, or there is a radical $A_3$ in the molecule in each case. These substituents are the radicals which produce the surface activity of the photoinitiator compounds, i.e. which ensure that the photoinitiator accumulates at the surface of the formulation that is to be cured.

The invention therefore also provides a process for producing coatings having stable scratch-resistant surfaces, in which
(1) a photocurable formulation comprising
   (A) an ethylenically unsaturated polymerizable compound; and
   (B) a photoinitiator;
is prepared;
(2) this formulation is applied to a substrate; and
(3) the formulation is cured either
   only by exposure to electromagnetic radiation with a wavelength ranging from 200 nm into the IR region, or
   by exposure to electromagnetic radiation with a wavelength ranging from 200 nm into the IR region and prior, simultaneous and/or subsequent exposure to heat;
wherein
the formulation comprises as photoinitiator (B) at least one surface-active photoinitiator of the formula Ia, Ib or Ic which accumulates at the surface of the formulation.

In accordance with the invention, the photoinitiators are used to cure free-radically polymerizable systems, the objective being to obtain a hardened surface having outstanding properties. For this objective to be achieved it is critical that the photoinitiator accumulates at the surface of the formulation to be cured. As has already been described above, this is achieved by means of appropriate substituents on the photoinitiator. However, an improvement in the surface properties is not only achievable using such initiators just in purely photocurable systems, but is also obtained in mixed thermally/photocurable formulations. The present invention therefore provides both for the use of the photoinitiators of the formula I in purely photocurable formulations and for the use of the photoinitiators of the formula I in mixed photochemically and thermally curable formulations. Thermal curing may take place before, during or after exposure to light.

The invention accordingly also provides a process as described above in which the photocurable formulation comprises as a further component at least one thermally crosslinkable compound (C) and is cured by exposure to light whose wavelength extends from 200 nm into the IR region and by prior, simultaneous and/or subsequent exposure to heat.

In accordance with the invention, the compounds of the formula Ia, Ib and Ic may be used as surface-active photo initiators for the photopolymerization of ethylenically unsaturated compounds or mixtures comprising such compounds, and undergo orientation toward the surface of the respective formulation. The invention thus also provides a method of causing a photoinitiator to accumulate at the surface of coatings, which comprises adding a surface-active photoinitiator of the formula Ia, Ib and Ic to the photopolymerizable mixture comprising the ethylenically unsaturated photopolymerizable compounds.

In accordance with the invention, the initiators of the formula (I) are not used in compositions which comprise siloxane-modified resin components if they are intended to be used as surface-active photoinitiators. The compounds of the invention are, however, also outstandingly suitable for increasing the miscibility and compatibility of the initiator molecule with corresponding siloxane-modified resins. Preference is given to the surface-active photoinitiator application. The photoinitiators may also be used in combination with other photoinitiators (E) and/or further additives (D).

The invention accordingly also provides photopolymerizable compositions comprising
(A) at least one ethylenically unsaturated free-radically photopolymerizable compound; and
(B) at least one surface-active photoinitiator of the formula Ia, Ib or Ic.

The invention further provides photopolymerizable compositions comprising
(A) at least one ethylenically unsaturated free-radically photopolymerizable compound;
(B) at least one surface-active photoinitiator of the formula Ia, Ib or Ic, and
(C) at least one thermally crosslinkable compound.

In accordance with the invention, the compositions may also comprise further, different photoinitiators (E) and/or further additives (D).

The addition of thermal crosslinking catalysts is also possible. Suitable examples are set out later on below.

The unsaturated compounds (A) may contain one or more olefinic double bonds. They may be of low (monomeric) or relatively high (oligomeric) molecular mass. Examples of monomers containing a double bond are alkyl or hydroxyalkyl acrylates or methacrylates, such as methyl, ethyl, butyl, 2-ethylhexyl or 2-hydroxyethyl acrylate, isobornyl acrylate, methyl methacrylate or ethyl methacrylate. Silicone acrylates are also of interest. Other examples are acrynitrile, acrylamide, methacrylamide, N-substituted (meth)acrylamides, vinyl esters such as vinyl acetate, vinyl ethers such as isobutyl vinyl ether, styrene, alkylstyrenes and halostyrenes, N-vinylpyrrolidone, vinyl chloride or vinylidene chloride.

Examples of monomers containing two or more double bonds are ethylene glycol, propylene glycol, neopentyl glycol, hexamethylene glycol and bisphenol A diacrylates, 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of relatively high molecular mass (oligomeric) polyunsaturated compounds are acrylated epoxy resins and acrylated or vinyl ether- or epoxy-functional polyesters, polyurethanes and polyethers. Further examples of unsaturated oligomers are unsaturated polyester resins, generally prepared from maleic acid, phthalic acid and one or more diols and having molecular weights of from about 500 to 3000. In addition to these it is also possible to use vinyl ether monomers and oligomers, and also maleate-terminated oligomers with polyester, polyurethane, polyether, polyvinyl ether and epoxide main chains. Especially suitable are combinations of polymers and oligomers which carry vinyl ether groups, as described in WO 90/01512. Also suitable, however, are copolymers of monomers functionalized with maleic acid and vinyl ether.

Also suitable are compounds containing one or more free-radically polymerizable double bonds. In these compounds the free-radically polymerizable double bonds are preferably in the form of (meth)acryloyl groups. (Meth) acryloyl and, respectively, (meth)acrylic here and below mean acryloyl and/or methacryloyl, and acrylic and/or methacrylic, respectively. Preferably, at least two polymerizable double bonds are present in the molecule in the form of (meth)acryloyl groups. The compounds in question may comprise, for example, (meth)acryloylunctional oligomeric and/or polymeric compounds of poly(meth) acrylate. The number-average molecular mass of this compound may be for example from 300 to 10 000, preferably from 800 to 10 000. The compounds preferably containing free-radically polymerizable double bonds in the form of (meth)acryloyl groups may be obtained by customary methods, for example by reacting poly(meth)acrylates with (meth)acrylic acid. These and other preparation methods are described in the literature and are known to the person skilled in the art.

Unsaturated oligomers of this kind may also be referred to as prepolymers.

Functionalized acrylates are also suitable. Examples of suitable monomers which are normally used to form the backbone (the base polymer) of such functionalized acrylate and methacrylate polymers are acrylate, methyl acrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate etc. Additionally, appropriate amounts of functional monomers are copolymerized during the polymerization in order to give the functional polymers. Acidunctionalized acrylate or methacrylate polymers are obtained using acid-functional monomers such as acrylic acid and methacrylic acid. Hydroxy-functional acrylate or methacrylate polymers are formed from hydroxy-functional monomers, such as 2-hydroxyethyl methacrylate, 2-hydroxypropyl methacrylate and 3,4-dihydroxybutyl methacrylate. Epoxy-functionalized acrylate or methacrylate polymers are obtained using epoxy-functional monomers such as glycidyl methacrylate, 2,3-epoxybutyl methacrylate, 3,4-epoxybutyl methacrylate, 2,3-epoxycyclohexyl methacrylate, 10,11-epoxyundecyl methacrylate etc. Similarly, for example, isocyanate-functionalized polymers may be prepared from isocyanate-functionalized monomers, such as meta-isopropenyl-α,α-dimethylbenzyl isocyanate, for example.

Particularly suitable compounds are, for example, esters of ethylenically unsaturated monofunctional or polyfunctional carboxylic acids and polyols or polyepoxides, and polymers containing ethylenically unsaturated groups in the chain or in side groups, such as unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of suitable monofunctional or polyfunctional unsaturated carboxylic acids are acrylic acid, methacrylic acid, crotonic acid, itaconic acid, cinnamic acid, maleic acid, fumaric acid, unsaturated fatty acids such as linolenic acid or oleic acid. Acrylic acid and methacrylic acid are preferred.

It is, however, also possible to use saturated dicarboxylic or polycarboxylic acids in a mixture with unsaturated carboxylic acids. Examples of suitable saturated dicarboxylic or polycarboxylic acids include tetrachlorophthalic acid, tetrabromophthalic acid, phthalic anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid, etc.

Suitable polyols include aromatic and especially aliphatic and cycloaliphatic polyols. Examples of aromatic polyols are hydroquinone, 4,4'-dihydroxybiphenyl, 2,2-di(4-hydroxyphenyl)propane, and also novolaks and resols. Examples of polyepoxides are those based on the aforementioned polyols, especially the aromatic polyols, and epichlorohydrin. Further suitable polyols include polymers and copolymers containing hydroxyl groups in the polymer chain or in side groups, such as polyvinyl alcohol and copolymers thereof or polyhydroxyalkyl methacrylates or copolymers thereof, for example. Oligoesters containing hydroxyl end groups are further suitable polyols.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(P-hydroxyethyl)amine, trimethylolethane, trimethylolpropane, pentaerythritol, dipentaerythritol and sorbitol.

The polyols may have been partly or fully esterified with one or more different unsaturated carboxylic acids, the free hydroxyl groups in partial esters possibly having been modified, e.g. etherified or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, modified pentaerythritol triacrylate, sorbitol tetramethacrylate, sorbitol pentaacrylate, sorbitol hexaacrylate, oligoester acrylates and methacrylates, glycerol diacrylate and triacrylate, 1,4-Cyclohexane diacrylate, bisacrylates and bismethacrylates of polyethylene glycol having a molecular weight from 200 to 1500, or mixtures thereof.

Suitable components (A) also include the amides of identical or different unsaturated carboxylic acids with aromatic, cycloaliphatic and aliphatic polyamines having preferably from 2 to 6, particularly from 2 to 4 amino groups. Examples of such polyamines are ethylenediamine, 1,2- or 1,3-propylenediamine, 1,2-, 1,3- or 1,4-butylenediamine, 1,5-pentylenediamine, 1,6- hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-amino-propoxy)ethane. Further suitable polyamines are polymers and copolymers containing possibly additional amino groups in the side chain, and oligoamides having amino end groups. Examples of such unsaturated amides are: methylenebisacrylamide, 1,6-hexamethylenebisacrylamide, diethylenetriaminetrismethacrylamide, bis(methacrylamidopropoxy)ethane, β-methacrylamidoethyl methacrylate, and N-[(β-hydroxyethoxy)ethyl]-acrylamide.

Suitable unsaturated polyesters and polyamides are derived, for example, from maleic acid and diols or diamines. The maleic acid may have been replaced in part by other dicarboxylic acids. They may be used together with ethylenically unsaturated comonomers, e.g. styrene. The polyesters and polyamides may also be derived from dicarboxylic acids and ethylenically unsaturated diols or diamines, especially from relatively long chain ones having, for example, from 6 to 20 carbon atoms. Examples of polyurethanes are those synthesized from saturated or unsaturated diisocyanates and unsaturated or saturated diols, respectively.

Polybutadiene and polyisoprene and copolymers thereof are known. Examples of suitable comonomers are olefins such as ethylene, propene, butene, hexene, (meth)acrylates, acrylonitrile, styrene or vinyl chloride. Polymers containg (meth)acrylate groups in the side chain are likewise known. They may comprise, for example, reaction products of novolak-based epoxy resins with (meth)acrylic acid, homopolymers or copolymers of vinyl alcohol or the hydroxyalkyl derivatives thereof that have been esterified with (meth)acrylic acid, or homopolymers and copolymers of (meth)acrylates esterified with hydroxyalkyl (meth) acrylates.

The photopolymerizable compounds (A) may be used alone or in any desired mixtures. Preference is given to using mixtures of polyol (meth)acrylates.

It is also possible to add binders to the compositions of the invention, which is especially appropriate when the photopolymerizable compounds are liquid or viscous substances. The amount of the binder can be for example 5–95, preferably 10–90 and especially 40–90% by weight, based on the overall solids. The choice of binder is made depending on the field of use and the properties required for that field, such as developability in aqueous and organic solvent systems, adhesion to substrates, and oxygen sensitivity, for example.

Examples of suitable binders are polymers having a molecular weight of approximately 5000–2 000 000, preferably 10 000–1 000 000. Examples are: homopolymeric and copolymeric acrylates and methacrylates, e.g. copolymers of methyl methacrylate/ethyl acrylate/methacrylic acid, poly(alkyl methacrylates), poly(alkyl acrylates); cellulose esters and cellulose ethers such as cellulose acetate, cellulose acetate butyrate, methylcellulose, ethylcellulose; polyvinylbutyral, polyvinylformal, cyclized rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly (ethylenelvinyl acetate), polymers such as polycaprolactam and poly(hexamethyleneadipamide), polyesters such as poly (ethylene glycol terephtalate) and poly(hexamethylene glycol succinate).

As component (A), i.e. UV-curable component, it is also possible to use the resins listed later on below under (C1). Examples of those that are of particular interest are unsaturated acrylates containing reactive functional groups. The reactive functional group may be selected, for example, from a hydroxyl, thiol, isocyanate, epoxide, anhydride, carboxyl, amino or a blocked amino group. Examples of OH-containing unsaturated acrylates are hydroxyethyl and hydroxybutyl acrylates or else glycidyl acrylates.

The unsaturated compounds may also be used in a mixture with non-photopolymerizable film-forming components. These may be, for example, physically drying polymers or their solutions in organic solvents, such as nitrocellulose or cellulose acetobutyrate, for example. They may also, however, be chemically and/or thermally curable resins, such as polyisocyanates, polyepoxides or melamine resins, for example. By melamine resins are meant not only condensates of melamine (cyanuric triamide) with carbonyl compounds, preferably with formaldehyde. Melamine resins are available commercially, under the tradename Cymel, for example.

The additional use of thermally curable resins is of importance for use in what are known as hybrid systems, which may be both photopolymerized and also thermally crosslinked.

Component (A) may comprise, for example, a coating composition comprising (A1) compounds containing one or more free-radically polymerizable double bonds and further containing at least one other functional group which is reactive in the sense of an addition reaction and/or condensation reaction (examples have been given above), (A2) compounds containing one or more free-radically polymerizable double bonds and further containing at least one other functional group which is reactive in a sense of an addition reaction and/or condensation reaction, the additional reactive functional group being complementary to or reactive toward the additional reactive functional groups of component (A1), (A3) if desired, at least one monomeric, oligomeric and/or polymeric compound containing at least one functional group which is reactive in the sense of an addition reaction and/or condensation reaction toward the functional groups from component (A1) or component (A2) that are present in addition to the free-radically polymerizable double bonds.

Component (A2) carries in each case the groups which are reactive toward or complementary to component (A1). In this context it is possible in each case for different kinds of functional groups to be present in one component. In component (A3) there is a further component available containing functional groups which are reactive in the sense of addition reactions and/or condensation reactions and which are able to react with the functional groups of (A1) or (A2) that are present in addition to the free-radically polymerizable double bonds. Component (A3) contains no free-radically polymerizable double bonds. Examples of such combinations of (A1), (A2), (A3) can be found in WO 99/55785. Examples of suitable reactive functional groups are selected, for example, from hydroxyl, isocyanate, epoxide, anhydride, carboxyl or blocked amino groups. Examples have been described above.

Constituents of component (C) are, for example, thermally curable coating system constituents that are customary in the art. Accordingly, component (C) may comprise two or more constituents.

Examples of component (C) are oligomers and/or polymers derived from α,β-unsaturated acids and derivatives thereof; examples are polyacrylates and polymethacrylates, and polyacrylonitriles, polyacrylamides and polymethyl methacrylates that have been impact-modified using butyl acrylate. Further examples of component (C) are urethanes, polyurethanes derived from polyethers, polyesters and polyacrylates containing free hydroxyl groups or thiol groups, on the one hand, and aliphatic or aromatic polyisocyanates, on the other, and also precursors thereof. Accordingly, component (C) also comprises, for example, crosslinkable acrylic resins derived from substituted acrylates, such as epoxy acrylates, urethane acrylates or polyester acrylates. It is also possible for alkyd resins, polyester resins and acrylic resins and their modifications, which are crosslinked with melamine resins, urea resins, isocyanates, isocyanurates, polyisocyanates, polyisocyanurates and epoxy resins, to be constituents of component (C).

Component (C) generally comprises for example, a film-forming binder based on a thermoplastic or thermosettable resin, predominantly on a thermosettable resin. Examples thereof are alkyd, acrylic, polyester, phenolic, melamine, epoxy and polyurethane resins and mixtures thereof. Examples of these are described, for example, in Ullmann's Encyclopedia of Industrial Chemistry, 5th Ed., Vol. A18, pp. 368–426, VCH, Weinheim 1991.

Component (C) may be a cold-curable or heat-curable binder, and the addition of a curing catalyst may be advantageous. Suitable catalysts which accelerate the curing of the binder are described, for example, in Ullmann's Encyclopedia of Industrial Chemistry, Vol. A18, p.469, VCH Verlagsgesellschaft, Weinheim 1991.

Examples of specific binders suitable as component (C) are 1. paints based on cold- or heat-crosslinkable alkyd, acrylate, polyester, epoxy or melamine resins or mixtures of such resins, with or without addition of a curing catalyst;
2. two-component polyurethane paints based on hydroxyl-containing acrylate, polyester or polyether resins and on aliphatic or aromatic isocyanates, isocyanurates or polyisocyanates;
3. two-component polyurethane paints based on thiol-functional acrylate, polyester or polyether resins and on aliphatic or aromatic isocyanates, isocyanurates or polyisocyanates;
4. one-component polyurethane paints based on blocked isocyanates, isocyanurates or polyisocyanates which are deblocked in the course of stoving; melamine resins may be added, if appropriate;
5. one-component polyurethane paints based on aliphatic or aromatic urethanes or polyurethanes and on hydroxyl-containing acrylate, polyester or polyether resins;
6. one-component polyurethane paints based on aliphatic or aromatic urethane acrylates or polyurethane acrylates having free amine groups in the urethane structure and on melamine resins or polyether resins, with or without addition of a curing catalyst;
7. two-component paints based on (poly)ketimines and on aliphatic or aromatic isocyanates, isocyanurates or polyisocyanates;
8. two-component paints based on (poly)ketimines and on an unsaturated acrylate resin or a polyacetoacetate resin or a methacrylamidoglycolate methyl ester;
9. two-component paints based on carboxyl- or amino-containing polyacrylates and polyepoxides;
10. two-component paints based on acrylate resins containing anhydride groups and on a polyhydroxy or polyamino component;
11. two-component paints based on acrylate-containing anhydrides and polyepoxides;
12. two-component paints based on (poly)oxazolines and on acrylate resins containing anhydride groups, or unsaturated acrylate resins or aliphatic or aromatic isocyanates, isocyanurates or polyisocyanates;
13. two-component paints based on unsaturated (poly)acrylates and (poly)malonates;
14. thermoplastic polyacrylate paints based on thermoplastic acrylate resins or externally crosslinking acrylate resins in combination with etherified melamine resins.

Blocked isocyanates as may be employed, inter alia, in component (C) are described, for example, in Organischer Metallschutz: Entwicklung und Anwendung von Beschichtungs-stoffen [Organic Protection of Metals: Development and Application of Coating Materials], page 159–160, Vincentz Verlag, Hannover (1993). These are compounds in which the highly reactive NCO group is "blocked" by reaction with specific radicals, such as primary alcohols, phenol, acetoacetates, F-caprolactam, phthalimide, imidazole, oxime or amine. The blocked isocyanate is stable in liquid systems and also in the presence of hydroxyl groups. On heating, the blocking agents are eliminated and the NCO group is exposed.

Both 1-Component (1K) and 2-Component (2K) systems may be used as component (C). Examples of such systems are described in Ullmann's Encyclopedia of Industrial Chemistry, Vol. A18, Paints and Coatings, page 404–407, VCH Verlagsgesellschaft mbH, Weinheim (1991).

The composition may be optimized by specially adapting the formulation, for example by varying the binder/crosslinker ratio. Such measures are well known to the person skilled in the art of coatings technology.

In the curing process of invention component (C) is preferably a mixture based on acrylate/melamine (and melamine derivatives), 2-Component polyurethane, 1-Component polyurethane, 2-Component epoxy/carboxy or 1-Component epoxy/carboxy. Mixtures of these systems are also possible, an example being the addition of melamine (or derivatives thereof) to 1-Component polyurethanes.

Component (C) is preferably a binder based on a polyacrylate with melamine or on a melamine derivative. Preference is also given to a system based on a polyacrylate polyol and/or polyester polyol with an unblocked polyisocyanate or polyisocyanurate.

Component (C) may further comprise monomeric and/or oligomeric compounds containing ethylenically unsaturated bonds (prepolymers) which additionally contain at least one or more OH, SH, $NH_2$, COOH, epoxy or NCO groups (=Cl) capable of reaction with the binder and/or crosslinker constituent of component (C). Following application and thermal curing, the ethylenically unsaturated bonds are converted by UV radiation into a crosslinked, high molecular mass form. Examples of such components (C) are described, for example, in the abovementioned publication Ullmann's Encyclopedia of Industrial Chemistry, 5th Ed., Vol. A18, pages 451–453, or by S. Urano, K. Aoki, N. Tsuboniva and R. Mizuguchi in Progress in Organic Coatings, 20 (1992), 471–486, or by H. Terashima and O. Isozaki in JOCCA 1992 (6), 222.

(C1) may be, for example, an OH-containing unsaturated acrylate, e.g. hydroxyethyl acrylate or hydroxybutyl acrylate or else glycidyl acrylates. Component (C1) may be of any desired construction (e.g. polyester, polyacrylate, polyether, etc., units) provided there are an ethylenically unsaturated double bond and also free OH, SH, COOH, $NH_2$, epoxy or NCO groups.

(C1) may also be obtained, for example, by reacting an epoxy-functional oligomer with acrylic acid or methacrylic acid. A typical example of an OH-functional oligomer containing vinylic double bonds is

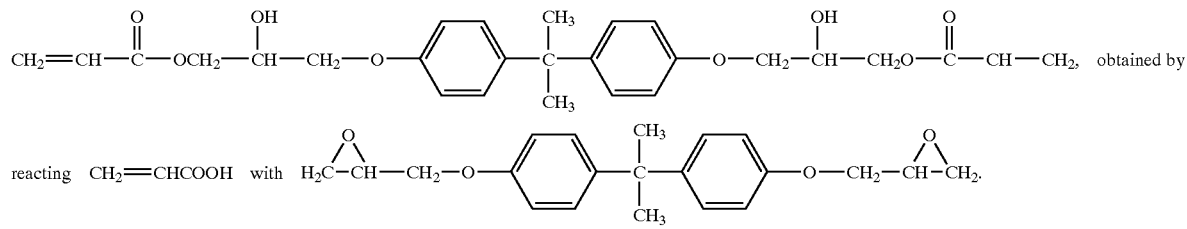

reacting $CH_2$=CHCOOH with

One possibility for preparing component (C1) is also, for example, the reaction of an oligomer that contains only one epoxy group and at another site in the molecule possesses a free OH group.

The ratio of components (A) to (C) in the UV-crosslinking and thermally crosslinking formulations is not critical. "Dual-cure" systems are well known to the person skilled in the art, who is therefore well aware of the optimum proportions of the UV-crosslinkable and thermally crosslinkable components for the particular desired application. For example, the compositions may comprise components (A) and (C) in a ratio of from 5:95 to 95:5, from 20:80 to 80:20 or from 30:70 to 70:30, e.g. from 40:60 to 60:40.

Examples of "dual-cure" systems, i.e. systems containing both UV-curable and thermally curable components, may be found, inter alia, in U.S. Pat. No. 5,922,473, columns 6 to 10.

To the compositions that are used in the process of the invention it is also possible to add solvents or water. Where the compositions are used without solvents, they comprise, for example, powder coating formulations. Suitable solvents are solvents which are known to the person skilled in the art and are customary particularly in coatings technology. Examples are various organic solvents, such as ketones, e.g. methyl ethyl ketone, cyclohexanone; aromatic hydrocarbons, e.g. toluene, xylene or tetramethylbenzene; glycol ethers, such as diethylene glycol monoethyl ether, dipropylene glycol diethyl ether; esters, such as ethyl acetate; aliphatic hydrocarbons, such as hexane, octane, decane; or petroleum solvents, such as petroleum ether.

The invention also provides compositions comprising as component (A) at least one ethylenically unsaturated photopolymerizable compound in emulsion or solution in water. Such radiation-curable aqueous prepolymer dispersions are available commercially in numerous variations. They are understood to comprise a dispersion of water and at least one prepolymer dispersed therein. The concentration of the water in these systems is, for example, from 5 to 80, in particular from 30 to 60% by weight. The radiation-curable prepolymer or prepolymer mixture is present, for example, in concentrations of from 95 to 20, in particular from 70 to 40% by weight. In these compositions the sum of the percentages stated for water and prepolymers is in each case 100; the auxiliaries and additives are extra in different amounts depending on the intended use.

The radiation-curable film-forming prepolymers which are in dispersion and often also in solution in water comprise monofunctional or polyfunctional ethylenically unsaturated prepolymers which are known per se for aqueous prepolymer dispersions, may be initiated by means of free radicals, and have a polymerizable double bond content of, for example, from 0.01 to 1.0 mol per 100 g of prepolymer and also have an average molecular weight of, for example, at least 400, in particular from 500 to 10 000. Depending on the intended application, however, prepolymers with higher molecular weights may also be suitable. Use is made, for example, of polyesters containing polymerizable C—C double bonds and having an acid number of not more than 10, polyethers containing polymerizable C—C double bonds, hydroxyl-containing reaction products of a polyepoxide containing at least two epoxide groups per molecule with at least one α,β-ethylenically unsaturated carboxylic acid, polyurethane (meth)acrylates, and also acrylic copolymers containing α,β-ethylenically unsaturated acrylic radicals, as described, for example, in EP 012339. Mixtures of these prepolymers may likewise be used. Examples of further suitable prepolymers include the polymerizable prepolymers described in EP 033896, which are thioether adducts of polymerizable prepolymers having an average molecular weight of at least 600, a carboxyl group content of from 0.2 to 15% and a polymerizable C—C double bond content of from 0.01 to 0.8 mol per 100 g of prepolymer. Other suitable aqueous dispersions based on specific alkyl (meth)acrylate polymers are described in EP 041125; suitable water-dispersible, radiation-curable prepolymers comprising urethane acrylates are given, for example, in DE 2936039.

As further additions, these radiation-curable aqueous prepolymer dispersions may comprise dispersing aids, emulsifiers, antioxidants, light stabilizers, dyes, pigments, fillers, e.g. talc, gypsum, silica, rutile, carbon black, zinc oxide, iron oxides, reaction accelerants, levelling agents, lubricants, wetting agents, thickeners, matting agents, defoamers, and other auxiliaries customary in coatings technology. Suitable dispersing aids include water-soluble organic compounds of high molecular mass containing polar groups, such as polyvinyl alcohols, polyvinylpyrrolidone or cellulose ethers. Emulsifiers which can be used include nonionic, and possibly also ionic, emulsifiers.

The compounds of the invention and mixtures thereof may also be used as free-radical photoinitiators or photoinitiating systems for radiation-curable powder coating materials. The powder coating materials may be based on solid resins and monomers containing reactive double bonds, such as maleates, vinyl ethers, acrylates, acrylamides and mixtures thereof. A free-radically UV-curable powder coating material may be formulated by mixing unsaturated polyester resins with solid acrylamides (e.g. methylacrylamidoglycolate methyl ester) and a free-radical photoinitiator of the invention, as described for example in the paper "Radiation Curing of Powder Coating", Conference Proceedings, Radtech Europe 1993 by M. Wittig and Th. Gohmann. Free-radically UV-curable powder coating materials may also be formulated by mixing unsaturated polyester resins with solid acrylates, methacrylates or vinyl ethers and a photoinitiator (or photoinitiator mixture) of the invention. The powder coating materials may also include binders, as described for example in DE 4228514 and EP 636669. The powder coating formulations described in EP 636669 contain, for example, a) an unsaturated resin from the group of the (semi)crystalline or amorphous unsaturated polyesters, unsaturated polyacrylates or mixtures thereof with unsaturated polyesters, particular preference being given to those derived from maleic acid or fumaric acid; b) an oligomeric or polymeric crosslinking agent containing vinyl ether-functional, vinyl ester-functional or (meth) acrylate-functional groups, particular preference being given to vinyl ether oligomers, such as divinyl ether-functionalized urethanes; c) the photoinitiator.

The UV-curable powder coating materials may also comprise white or coloured pigments. For example, preferably rutile titanium dioxide may be used in concentrations of up to 50% by weight in order to give a cured powder coating possessing good hiding power. The technique normally involves applying the powder to the substrate, such as metal or wood, by electrostatic or tribostatic spraying, melting the powder by heating and, after a smooth film has formed, radiation-curing the coating with ultraviolet and/or visible light, using medium-pressure mercury lamps, metal halide lamps or xenon lamps, for example. A particular advantage of the radiation-curable powder coating materials over their thermally curable counterparts is that the flow time after melting of the powder particles may be selectively extended in order to ensure the formation of a smooth, highly glossy coating. Unlike thermally curable systems, radiation-curable powder coating materials may be formulated without the unwanted effect of a shortened lifetime in such a way that they melt at relatively low temperatures. For this reason they are also suitable as coatings for heat-sensitive substrates, such as wood or plastics.

Where the powder coating materials are not to be applied to heat-sensitive substrates, as in the case of metals (vehicle coatings), however, it is also possible to provide dual-cure powder coating formulations with the photoinitiators of the invention. Such formulations are known to the person skilled in the art; they are cured both thermally and by means of UV. Formulations of this kind are given, for example, in U.S. Pat. No. 5,922,473.

Besides the photoinitiators of the invention, the powder coating formulations may also comprise UV absorbers. Appropriate examples are listed later on below.

Besides the photoinitiator, the photopolymerizable mixtures may comprise various additives (D). Examples of these are thermal inhibitors, which are intended to prevent premature polymerization, such as 2,2,6,6-tetramethyl-4-hydroxypiperidin-1-oxyl (4-hydroxy-TEMPO) and derivatives thereof, such as bis(2,2,6,6-tetramethylpiperidin-1-oxyl-4-yl) decanedioate or polyalkyl-piperidine-N-oxyl radicals, 3-arylbenzofuran-2-one and derivatives thereof, such as 5,7-di-tert-butyl-3-phenyl-3H-benzofuran-2-one (as in international application No. PCT/EP00/12165 dated Apr. 12, 2000 for example), hydroquinone, hydroquinone derivatives, p-methoxyphenol, β-naphthol or sterically hindered phenols such as 2,6-di(tert-butyl)-p-cresol. To increase the dark storage stability it is possible to use copper compounds, such as copper naphthenate, copper stearate or copper octoate, phosphorus compounds, such as triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, such as N-diethylhydroxylamine, for example. For the purpose of excluding atmospheric oxygen in the course of the polymerization it is possible to add paraffin or similar wax-like substances, which at the beginning of polymerization migrate to the surface, on account of their poor solubility in the polymer, where they form a transparent surface layer which prevents the ingress of air. Similarly, it is possible to apply an oxygen-impermeable layer. Light stabilizers which can be added include UV absorbers, such as those of the hydroxyphenylbenzotriazole, hydroxyphenylbenzophenone, oxalmide or hydroxyphenyl-s-triazine type. These compounds may be used individually or in mixtures, with or without the use of sterically hindered amines (HALS).

Examples of such UV absorbers and light stabilizers are
1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)-benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)-benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$]$_2$— where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole.
2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.
3. Esters of substituted and unsubstituted benzoic acids, for example 4-tert-butyl-phenyl salicylate, phenyl salicylate, octylphenyl salicylate, dibenzoyl resorcinol, bis(4-tert-butyl-benzoyl) resorcinol, benzoyl resorcinol, 2,4-di-tert-butylphenyl 3,5-di-tert-butyl-4-hydroxy-benzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.
4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

5. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl) hexamethylenediamine and 4-morpholino-2,6-dichloro-1,3,5-triazine, the condensate of 2-chloro-4,6-bis(4n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylaminoxethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4.5]decane, a reaction product of 7,7,9,9-tetramethyl-2-cycloundecyl-1-oxa-3,8-diaza-4-oxospiro[4.5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl4-aminopiperidine or 1,2,2,6,6-pentamethyl-4-aminopiperidine.

6. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy) phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl) pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-1,2H-dibenzo[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenzo[d,g]-1,3,2-dioxaphosphocin, 2,2',2"-nitrilo[triethyl tris(3,3',5,5'-tetra-tert-butyl-1,1'-biphenyl-2,2'-diyl)phosphite], 2-ethylhexyl 3,3',5,5'-tetra-tert-butyl-1,1'-biphenyl-2,2'-diylphosphite, 5-butyl-5-ethyl-2-(2,4,6-tri-tert-butylphenoxy)-1,3,2-dioxaphosphirane.

Furthermore, it is possible to use additives customary in the art, such as antistatics, flow improvers and adhesion promoters.

The photoinitiators of the formula Ia, Ib and Ic which have been provided with the group A or $A_3$ may also function as flow improvers, since they undergo orientation towards the surface and, because of the siloxane radical, are one of the influences on the surface properties. Further flow improvers customary in the art may also be added. Examples thereof are siloxane compounds or fluorohydrocarbon compounds or polyacrylates as are diversely available commercially.

The invention further provides for the use of compounds of the formula Ia, Ib and Ic as flow improvers, alone or in combination with further, customary flow improvers.

DIN 55945 defines levelling as "the more or less pronounced capacity of a still-liquid coating itself to compensate the unevennesses which arise in the course of its application." (cf. J. Bieleman, Lackadditive [Additives for Coatings], VCH Weinheim 1998, chapter 6). The levelling of a coating material depends greatly on its flow behaviour and on its surface tension. Flow improvers are substances which help wet coatings to become films which flow out evenly, by reducing the viscosity and/or surface tension. In the case of powder coating materials, flow improvers also lower the melt viscosity and the glass transition temperature and have an additional devolatilizing effect. Flow improvers are used to eliminate levelling defects or surface defects which detract from the overall appearance of the coating. Levelling defects or surface defects include the orange peel effect, formation of structures, cratering, fisheyes, sensitivity to draughts, substrate wetting problems, brush marks, runs, bittiness, pinholes, etc. The use of the compounds of the invention as flow improvers makes it possible to lower the surface tension. The surface tension may be calculated by determining the marginal angle of a drop of liquid on a surface (contact angle measurement).

In order to accelerate the photopolymerization it is possible to add, as further additives (D), amines, such as triethanolamine, N-methyldiethanolamine, 3,5-dimethoxybenzyl octaldecylcarbamate, 2-nitrobenzyl octadecylcarbamate, ethyl p-dimethylaminobenzoate, or Michler's ketone. Further suitable additives include capped amino compounds as described in the European patent EP-B 0 764 698. The effect of the amines may be boosted by adding aromatic ketones of the benzophenone type. Examples of amines which can be used as oxygen scavengers are substituted N,N-dialkylanilines, as described in EP 339841. Further accelerators, coinitiators and autoxidizers are thiols, thioethers, disulfides and phosphines, as described for example in EP 438123 and GB 2180358.

It is also possible to add chain transfer reagents customary in the art to the compositions of the invention. Examples are mercaptans, amines and benzothiazohle.

The photopolymerization may further be accelerated by adding photosensitizers as further additives (D), which shift or broaden the spectral sensitivity. These photosensitizers are, in particular, aromatic carbonyl compounds such as benzophenone derivatives, thioxanthone derivatives, and also especially isopropylthioxanthone, anthraquinone derivatives and 3-acylcoumarin derivatives, terphenyls, styryl ketones, and also 3-(aroylmethylene)thiazolines, camphorquinone, and also eosine dyes, rhodamine dyes and erythrosine dyes. The amines indicated above, for example, may also be regarded as photosensitizers.

The curing process, especially of compositions which are pigmented (with titanium dioxide for example), may also be assisted by adding an additional additive (D) which is a component which under thermal conditions forms free radicals, such as an azo compound, for instance 2,2'-azobis (4-methoxy-2,4-dimethylvaleronitrile), a triazene, diazo sulfide, pentazadiene or a peroxy compound such as hydroperoxide or peroxycarbonate, e.g. t-butyl hydroperoxide, as described for example in EP 245639.

As further additives (D), the compositions may also comprise, for example, a photoreducible dye, such as xanthene, benzoxanthene, benzothioxanthene, thiazine, pyronine, porphyrin or acridine dyes, and/or a radiation-cleavable trihalomethyl compound. Similar compositions are described, for example, in EP 445624.

Further common additives (D)—depending on the intended use—include optical brighteners, fillers, e.g. kaolin, talc, barytes, gypsum, chalk or silicatic fillers, pigments, dyes, wetting agents or flow improvers.

For the curing of thick and pigmented coatings it is appropriate to add glass microbeads or pulverized glass fibres, as described for example in U.S. Pat. No. 5,013,768.

The formulations may also comprise dyes and/or white or coloured pigments. Depending on the intended application, both organic and inorganic pigments may be used. Such additions are known to the person skilled in the art; some examples are titanium dioxide pigments, of, for example, the rutile or anatase type, carbon black, zinc oxide, such as zinc white, iron oxides, such as yellow iron oxide, red iron oxide, chrome yellow, chrome green, nickel titanium yellow, ultramarine blue, cobalt blue, bismuth vanadate, cadmium yellow or cadmium red. Examples of organic pigments are monoazo or disazo pigments, and also metal complexes thereof, phthalocyanine pigments, polycyclic pigments, such as perylene, anthraquinone, thioindigo, quinacridone or triphenylmethane pigments, and also diketopyrrolopyrrole, isoindolinone, e.g. tetrachloroisoindolinone, isoindoline, dioxazine, benzimidazolone and quinophthalone pigments.

The pigments may be used individually or else in a mixture in the formulations. Depending on the intended use, the pigments are added to the formulations in the amounts customary in the art, for example in an amount of from 1 to 60% by weight, or from 10 to 30% by weight, based on the overall mass.

The formulations may also, for example, comprise organic dyes from a very wide variety of classes. Examples are azo dyes, methine dyes, anthraquinone dyes or metal complex dyes. Customary concentrations are, for example, from 0.1 to 20%, in particular from 1 to 5%, based on the overall mass.

The choice of additives is guided by the respective field of application and by the properties desired for this field. The above-described additives (D) are customary in the art and, accordingly, are used in the amounts that are customary in the art.

In certain cases it may be of advantage to use mixtures of two or more of the photoinitiators of the formula Ia, Ib and/or Ic; it is advantageous, for example, to use mixtures obtained directly in the preparation. It is of course also possible to use mixtures with known photoinitiators (E), examples being mixtures with camphorquinone, benzophenone, benzophenone derivatives, acetophenone, acetophenone derivatives, such as α-hydroxycycloalkyl phenyl ketones or 2-hydroxy-2-methyl-1-phenylpropanone, dialkoxyacetophenones, α-hydroxy- or α-aminoacetophenones, such as (4-methylthiobenzoyl)-1-methyl-1-morpholinoethane, (4-morpholinobenzoyl)-1-benzyl-1-dimethylaminopropane, 4-aroyl-1,3-dioxolanes, benzoin alkyl ethers and benzil ketals, such as benzil dimethyl ketal, phenylglyoxalates and derivatives thereof, dimeric phenylglyoxalates, peresters, for example benzophenonetetracarboxylic peresters as described for example in EP 126541, monoacylphosphine oxides, such as (2,4,6-trimethylbenzoyl)phenylphosphine oxide, bisacylphosphine oxides, such as bis(2,6-dimethoxybenzoyl)(2,4,4-trimethylpent-1-yl)phosphine oxide, bis(2,4,6-trimethylbenzoyl)phenylphosphine oxide or bis(2,4,6-trimethylbenzoyl)(2,4-dipentoxyphenyl)phosphine oxide, trisacylphosphine oxides, halomethyltriazines, e.g. 2-[2-(4-methoxyphenyl)vinyl]4,6-bistrichloromethyl[1,3,5]triazine, 2-(4-methoxyphenyl)-4,6-bistrichloromethyl[1,3,5]triazine, 2-(3,4-dimethoxyphenyl)-4,6-bistrichloromethyl[1,3,5] triazine, 2-methyl-4,6-bistrichloromethyl[1,3,5]triazine, hexaarylbisimidazole/coinitiator systems, e.g. ortho-chlorohexaphenylbisimidazole together with 2-mercaptobenzothiazole, ferrocenium compounds or titanocenes, such as dicyclopentadienylbis(2,6-difluoro-3-pyrrolophenyl)titanium or borate photoinitiators. Where the photoinitiators of the invention are employed in hybrid systems, i.e. systems which can be cured both free-radically and cationically, use is made, in addition to the free-radical curing agents of the formula I and any further free-radical curing agents, of cationic photoinitiators such as benzoyl peroxide (other suitable peroxides are described in U.S. Pat. No. 4,950,581, column 19, lines 17–25), aromatic sulfonium, phosphonium or iodonium salts, as described for example in U.S. Pat. No. 4,950,581, column 18, line 60 to column 19, line 10.

The photopolymerizable compositions contain the photoinitiator appropriately in an amount of from 0.05 to 15% by weight, preferably from 0.1 to 5% by weight, based on the composition.

The stated amount of photoinitiator is based on the sum of all of the added photoinitiators, if mixtures thereof are used, i.e. both on the photoinitiator (B) and on the photoinitiators (B)+(E).

The photopolymerizable compositions may be used for a variety of purposes: for example, as a printing ink, as a clearcoat material, as a white paint, as a chromatically pigmented paint, for wood or metal, for example, as powder coating materials, as coating material for, inter alia, paper, wood, metal or plastic, as a daylight-curable coating for the marking of buildings and roads, for photographic reproduction techniques, for holographic recording materials, for image recording techniques or for producing printing plates which can be developed with organic solvents or using aqueous alkalis, for producing masks for screen printing, as dental filling compounds, as adhesives, including pressure-sensitive adhesives, as laminating resins, as etch resists or permanent resists, both liquid and in the form of dry films, as photostructurable dielectrics, and as solder resists for electronic circuits, as resists for producing colour filters for any type of screen, or for producing structures in the production process of plasma displays and eletroluminescent displays, for the production of optical switches, optical lattices (interference grids), for the production of three-dimensional articles by mass curing (UV curing in transparent moulds) or by the stereolithography process, as described for example in U.S. Pat. No. 4,575,330, for producing composite materials (e.g. styrenic polyesters which may where appropriate contain glass fibres and/or other fibres and other auxiliaries), and of gel coats and high-film-build compositions, for the coating or sealing of electronic components, or as coatings for optical fibres. The compositions are suitable, furthermore, for the production of optical lenses, e.g. contact lenses or Fresnel lenses, and also for producing medical instruments, aids or implants.

The compositions may also be used to produce gels having thermotropic properties, as described for example in DE 19700064 and EP 678534.

The compounds of the formula Ia, Ib and Ic may additionally be used as initiators for emulsion, bead or suspension polymerizations or as initiators in a polymerization for the fixing of states of order of liquid-crystalline monomers and oligomers, or as initiators for the fixing of dyes on organic materials.

The photocurable compositions of the invention are suitable, for example, as coating materials for substrates of all kinds, e.g. wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$, to which a protective coat or—by imagewise exposure—an image is to be applied.

The substrates may be coated by applying a liquid composition, a solution or suspension to the substrate. The choice of solvent and the concentration are guided primarily by the nature of the composition and by the coating technique. The solvent should be inert, i.e. it should not enter into any chemical reaction with the components and it should be able to be removed again in the course of drying after coating. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-metboxyethanol, 2-ethoxyethanol, 1-methoxy-2-propanol, 1,2-dimethoxyethane, ethyl acetate, n-butyl acetate and ethyl 3-ethoxypropionate.

The formulation is applied uniformly to a substrate by means of known coating techniques, for example by spincoating, dipping, knife coating, curtain coating techniques, brush application, spraying, especially by electrostatic spraying, and reverse roll coating, and also by electrophoretic deposition. It is also possible to apply the photosensitive layer to a temporary flexible support and then, by layer transfer via lamination, to the final substrate.

The application rate (coat thickness) and nature of the substrate (coat support) are dependent on the desired field of application. The dry film thickness range generally embraces values from about 0.1 $\mu$m to more than 100 $\mu$m, preferably from 0.02 to 2 $\mu$M.

A further field of use of photocuring is that of metal coating, as in the coating of metal sheets and tubes, cans or bottle closures, for example, and also photocuring on polymer coatings, for example PVC-based wall or floor coverings.

Examples of the photocuring of paper coatings are the colourless varnishing of labels, record sleeves or book covers.

The photosensitivity of the compositions of the invention generally ranges from about 200 nm to about 600 nm (UV region). Suitable radiation is present, for example, in sunlight or light from artificial sources. Light sources employed therefore include a large number of a very wide variety of types. Both point sources and arrays (lamp carpets) are suitable. Examples are carbon arc lamps, xenon arc lamps, medium-, high- and low-pressure mercury lamps, possibly doped with metal halides (metal-halogen lamps), microwave-excited metal vapour lamps, excimer lamps, superactinic fluorescent tubes, fluorescent lamps, argon incandescent lamps, flashlights, photographic floodlamps, light-emitting diodes (LEDs), electron beams and X-rays. The distance between the lamp and the substrate to be exposed may vary depending on the intended application and the type and output of the lamps, for example between 2 cm and 150 cm. Particularly suitable are laser light sources, for example excimer lasers such as krypton F lasers for exposure at 248 nm. Lasers in the visible range may also be used.

As already mentioned, curing in the process of the invention may take place solely by exposure to electromagnetic radiation. Depending on the composition of the formulation to be cured, however, thermal curing before, during or after radiation exposure is appropriate. Thermal curing takes place in accordance with methods known to the person skilled in the art. Curing is generally carried out in an oven, e.g. a forced-air oven, on a hotplate, or by irradiation using IR lamps. Curing without auxiliaries at room temperature is likewise possible, depending on the binder system used. The curing temperatures are generally between room temperature and 150° C., e.g. 25–150° C. or 50–150° C. In the case of powder coating materials or coil coating materials, the curing temperatures may also be higher, e.g. up to 350° C.

Where the formulation includes thermally curable components (C), it is additionally possible in accordance with the invention to add thermal drying catalysts or curing catalysts to the formulation as additional additives (D). Examples of possible drying catalysts, or thermal curing catalysts, are organometallic compounds, amines and/or phosphines. Organometallic compounds are, for example, metal carboxylates, especially those of the metals Pb, Mn, Co, Zn, Hf, Zr or Cu, or metal chelates, especially those of the metals Al, Hf, Ti or Zr, or organomnetallic compounds such as organotin compounds. Examples of metal carboxylates are the stearates of Pb, Mn or Zn, the octoates of Co, Zn or Cu, the naphthenates of Mn and Co or the corresponding linoleates or tallates. Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate and the alkoxides of these metals. Examples of organotin compounds are dibutyltin oxide, dibutyltin dilaurate and dibutyltin dioctoate. Examples of amines are, in particular, tertiary amines, such as tributylamine, triethanolamine, N-methyldiethanolamine, N-dimethylethanolamine, N-ethylmorpholine, N-methylmorpholine or diazabicyclooctane (triethylenediamine) and also the salts thereof. Further examples are quaternary ammonium salts, such as trimethylbenzylammonium chloride. As curing catalysts it is also possible to use phosphines, such as triphenylphosphine. Suitable catalysts are described, for example, as well in J. Bieleman, Lackadditive [Additives for Coatings], Wiley-VCH Verlag GmbH, Weinheim, 1998, page 244–247. Examples are sulfonic acids, such as p-toluenesulfonic acid, dodecylbenzenesulfonic acid, dinonylnaphthalenesulfonic acid or dinonyinaphthalenedisulfonic acid. For example, it is also possible to use latent or blocked sulfonic acids, where the blocking of the acid may be ionogenic or non-ionogenic.

Such catalysts are used in the concentrations known to the person skilled in the art and customary in that art.

The invention also provides a process for photopolymerizing non-volatile monomeric, oligomeric or polymeric compounds containing at least one ethylenically unsaturated double bond, which comprises exposing a composition as described above to electromagnetic radiation in the range from 200 to 600 nm.

The invention additionally provides for the use of the above-described composition and a process for producing pigmented and unpigmented paints and varnishes, powder coating materials, gel coats, composite materials or glass fibre cable coatings.

The invention likewise provides a coated substrate coated on at least one surface with a composition as described above.

The examples which follow illustrate the invention, but do not indicate any intention that the invention be restricted to the examples. As in the remainder of the description and in the claims, parts and percentages are by weight unless indicated otherwise. References to alkyl radicals containing more than three carbon atoms without indication of the isomer should be understood in each case as referring to the n-isomers

EXAMPLE 1

Preparation of

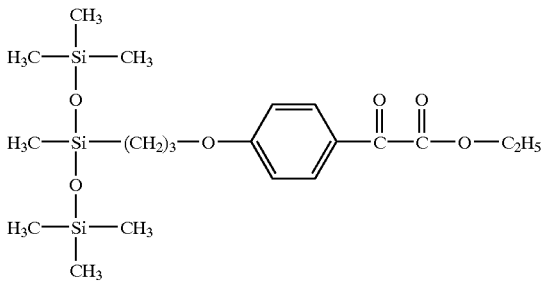

Compound of the formula Ia in which
Y is ethyl;
R is a radical of the formula II where $R_3$, $R_4$, $R_6$, $R_7$=H and $R_5$=AX;
A is a radical of the formula III where n=1, m=0, p=0; $G_1$=—O—Si(CH$_3$)$_2$, $G_2$=—Si(CH$_3$)$_3$;
X is —(CH$_2$)$_3$—O—.

a) Preparation of Ethyl 4-hydroxymandelate

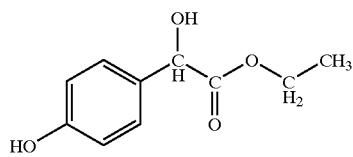

A mixture of 5 g of 4-hydroxymandelic acid and 1.28 g of p-toluenesulfonic acid in 200 ml of ethanol is heated at 50° C. for 4 hours. The mixture is poured into saturated aqueous NaHCO$_3$ solution, and a white precipitate is formed. The mixture is diluted with water until the precipitate disintegrates, and then is extracted with diethyl ether. The organic phases are dried over sodium sulfate. Filtration and evaporation of the solvent give ethyl 4-hydroxymandelate (4.2 g, 82%) as a pale yellowish solid.

$^1$H NMR (d$_6$-DMSO) δ [ppm]: 7.14 (d, 2H arom.); 6.72 (d, 2H arom.); 5.81 (br. d, 1H, —OH); 4.96 (br. d, 1H, -Ph-CH(OH)—C(O)); 4.05 (m, 2H, —C(O)—O—CH$_2$—CH$_3$); 3.34 (s, 1H, —OH); 1.12 (t, 3H, —C(O)—O—CH$_2$—CH$_3$).

b) Preparation of Ethyl 4-hydroxybenzoylformate

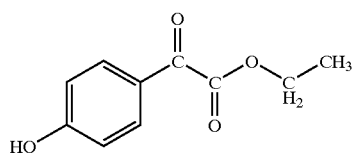

15.3 g of chromium trioxide is added dropwise to a solution of 15 g of ethyl 4-hydroxymandelate in 240 ml of acetic acid. The mixture is stirred at room temperature for 2 hours, poured into 1 l of ethyl acetate and extracted with saturated aqueous $Na_2CO_3$ solution. The aqueous phases are extracted with methylene chloride. The organic phases are washed with saturated aqueous $Na_2CO_3$ solution, followed by washing with water. The organic phases are dried over sodium sulfate. Filtration, evaporation of the solvent and distillation (ball-tube still distillation, boiling point 205° C. (0.076 bar)) give 4.04 g (27 wt %) ethyl 4-hydroxybenzoylformate as a yellow solid.

$^1$H NMR (CDCl$_3$) δ [ppm]: 7.95 (d, 2H arom.); 6.91 (d, 2H arom.); 6.07 (br. s, 1 OH, HO-Ph); 4.42 (q, J=7.2, 2H, —C(O)—O—C$\underline{H}_2$—CH$_3$); 1.40 (t, J=7.2, 3H, —C(O)—O—CH$_2$—C$\underline{H}_3$).

c) Preparation of Ethyl 4-allyloxybenzoylformate

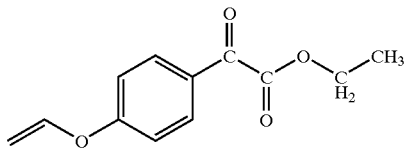

1.62 g (8.39 mmol) ethyl 4-hydroxybenzoylformate and 5.79 g (42 mmol) $K_2CO_3$ are dissolved in 70 ml acetone. 1.22 g (10.1 mmol) allyl bromide is added dropwise at room temperature. The mixture is heated at 40° C. for 3.25 hours under nitrogen atmosphere. The mixture is then filtered and evaporated. The phases are separated and water is extracted with toluene. The organic phases are dried over magnesium sulfate. Evaporation of the solvent and chromatography (eluent: hexane ethyl acetate 3:1) give 1.39 g (71 wt %) of a yellow oil.

$^1$H NMR (CDCl$_3$) δ [ppm]: 8.02 (d, 2H arom.); 6.99 (d, 2H arom.); 6.05 (m, 1H, CH$_2$=C$\underline{H}$—CH$_2$—O—); 5.40 (m, 2H, C$\underline{H}_2$=CH—CH$_2$—O—); 4.64 (m, 2H, CH$_2$=CH—CH$_2$—O—); 4.44 (q, J=7.2, 2H, —C(O)—O—C$\underline{H}_2$—CH$_3$); 1.43 (t, J=7.2, 3H, —C(O)—O—CH$_2$—C$\underline{H}_3$).

d) Preparation of the Inventive Product

A mixture of one equivalent of ethyl 4-allyloxybenzylformate (step c) and one equivalent of 1,1,1,3,5,5,5-heptamethyltrisiloxane in toluene is heated under reflux for 6.5 hours in the presence of 0.004 equivalent (120 ppm, based on the Pt content) of a carbon-supported Pt catalyst. The mixture is then filtered through silica gel. Filtration and evaporation of the solvent give 0.89 g (81 wt %) of the inventive compound in the form of an oil.

$^1$H NMR (CDCl$_3$) δ [ppm]: 7.87 (m, 2H arom.); 6.86 (m, 2H arom.); 4.35 (q, J=4, 2H, —C(O)—O—CH$_2$); 3.91 (t, J=8, 2H, —C$\underline{H}_2$—O—C$_6$H$_4$—); 1.74 (m, 2H, —Si—CH$_2$—C$\underline{H}_2$—CH$_2$—O—C$_6$H$_4$—); 1.32 (t, J=8, 3H, —C(O)—O—CH$_2$C$\underline{H}_3$); 0.48 (m, 2H, —Si—C$\underline{H}_2$—CH$_2$—CH$_2$—O—C$_6$H$_4$—); 0.03 (m, 21H, 7 Si—CH$_3$). m/z (EI+CI) 456 (M$^+$); according to the mass spectrum, a small amount of a further compound is also present:

458 (M$^+$); 456 (M$^+$); 414 (M$^+$); 236 (M$^+$); 194 (M$^+$):

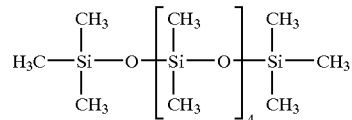

M = 458

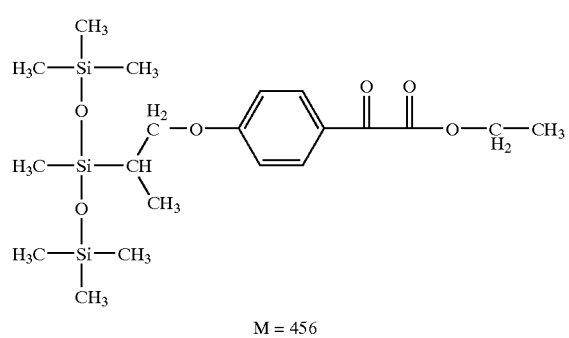

M = 456

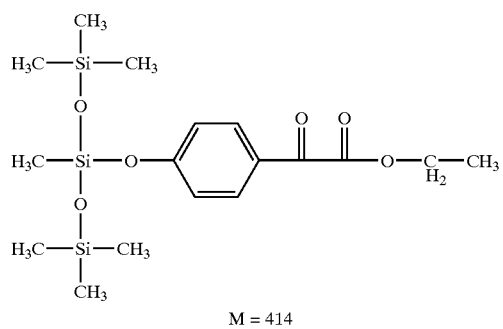

M = 414

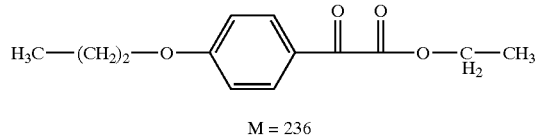

M = 236

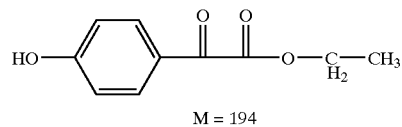

M = 194

EXAMPLE 2

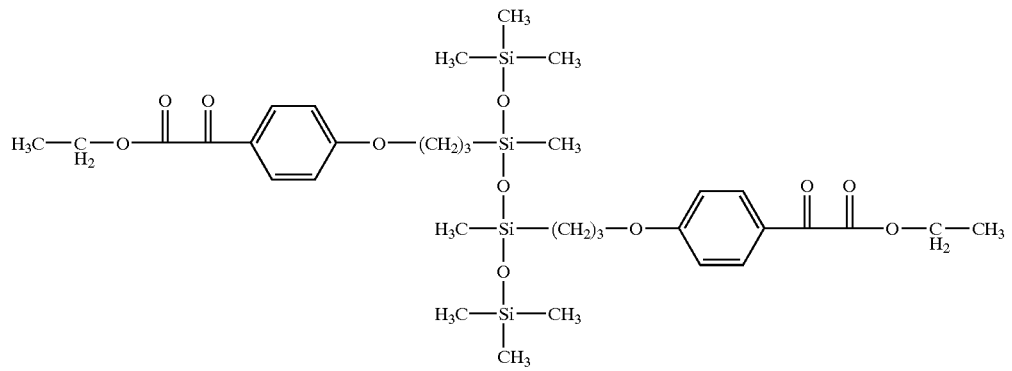

Compound of the formula Ia in which
Y is ethyl;
R is a radical of the formula II where $R_3$, $R_4$, $R_6$, $R_7$=H and $R_5$=AX;
A is a radical of the formula III where n=2, m=0, p=0; $G_1$=—O—Si(CH$_3$)$_2$, $G_2$=—Si(CH$_3$)$_3$;
X is —(CH$_2$)$_3$—O—.

The compound of example 2 is prepared by the method described in Example 1, using 2 mole equivalents of ethyl 4-allyloxybenzoylformate (Ex. 1 c) and 1.1 mole equivalent of 1,1,1,3,5,7,7,7-octamethyltetrasiloxane.

$^1$H NMR (CDCl$_3$) δ [ppm]: 7.86 (m, 2×2H arom.); 6.83 (m, 2×2H arom.); 4.35 (q, J=6, 2×2H, 2 —C(O)—O—CH$_2$); 3.97 (m, 2×2H, 2 —C<u>H</u>$_2$—O—C$_6$H$_4$—); 1.73 (m, 2×2H, 2 —Si—CH$_2$—C<u>H</u>$_2$—CH$_2$—O—C$_6$H$_4$—); 1.30 (t, J=6, 2×3H, 2 —C(O)—O—CH$_2$C<u>H</u>$_3$); 0.52 (m, 2×2H, 2 —Si—C<u>H</u>$_2$—CH$_2$—CH$_2$—O—C$_6$H$_4$—); 0.01 (m, 24H, 8 Si—CH$_3$); according to the mass spectrum, a small amount of a further compound is also present:

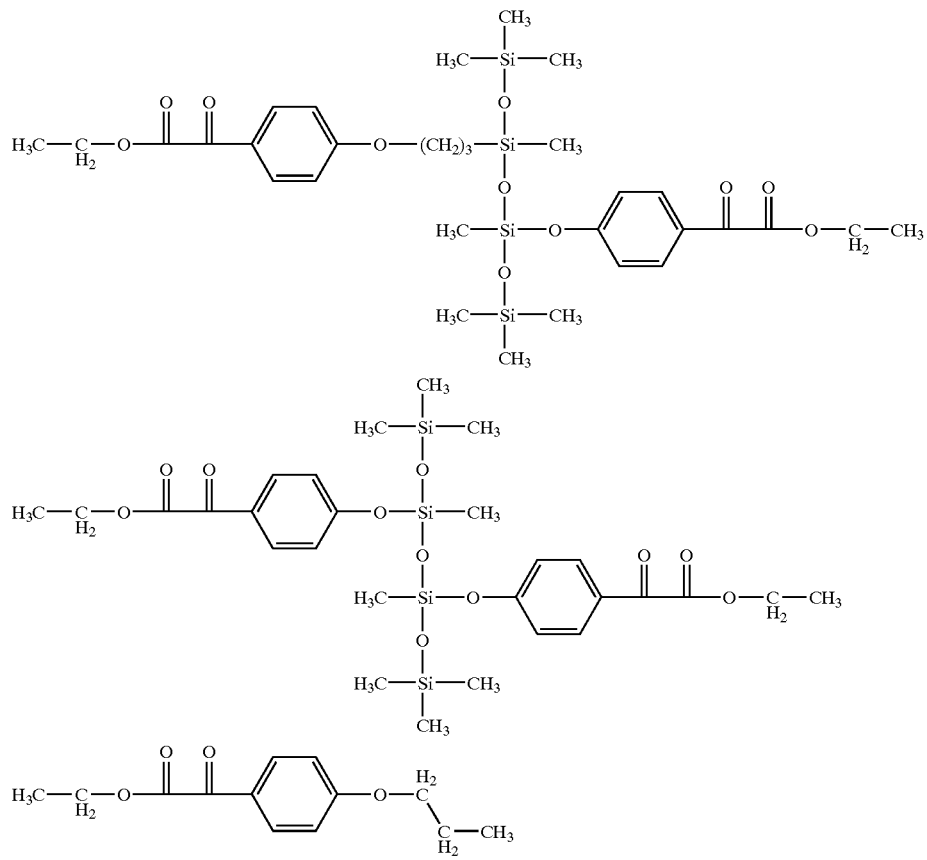

EXAMPLE 3

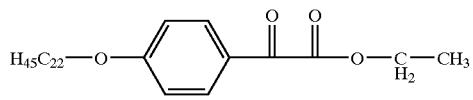

Compound of the formula Ia in which
Y is ethyl;
R is a radical of the formula II where $R_3$, $R_4$, $R_6$, $R_7$=H and $R_5$=AX;
A is $A_0$=—$C_{22}H_{45}$
X is —O—.

A solution of 0.35 g (1.80 mmol) ethyl 4-hydroxybenzoylformate, 0.77 g (1.98 mmol) Bromdocosane and 0.27 g (1.98 mmol) $K_2CO_3$ in 6 ml acetone is heated under reflux over night. The mixture is filtered and evaporated. Recrystallisation (ethanol) give 252 mg (28 wt %) of a solid. Mp=62–63° C.

EXAMPLE 4

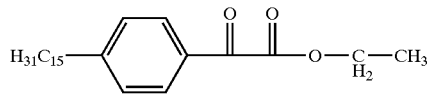

Compound of the formula Ia in which
Y is ethyl;
R is a radical of the formula II where $R_3$, $R_4$, $R_6$, $R_7$=H and $R_5$=AX;
A is $A_0$=—$CH_{15}H_{31}$;
X is a single bond.

A solution of 10 g of pentadecylbenzene and 7.1 g of oxalic acid monomethyl ester chloride in 7 ml of chloroform is added dropwise to a suspension of 6.93 g of aluminium trichloride in 14 ml of chloroform at around 0° C. The rate of addition is regulated so that the temperature of the mixture is held between 0° C. and 5° C. The mixture is stirred at 0° C. for 1 hour and then at room temperature for 4.5 hours. The mixture is poured into ice/water (200 ml) and extracted with ether. The organic phases are washed with saturated aqueous $NaHCO_3$ solution and water and dried over magnesium sulfate. Filtration, evaporation of the solvent and chromatography (eluent: hexane/methylene chloride 1:1) give the product (8.95 g, 66%) in the form of a pale yellowish solid.

U.V. ($CH_3CN$) max. at 267 nm ($\epsilon$ 15'921). $^1$H-NMR ($CDCl_3$) δ [ppm]: 7.93 (m, 2H arom.); 7.30 (m, 2H arom.); 4.44 (system AB, 2H, —$CH_2O$—); 2.68 (t, J=7.6, 2H, —$C_6H_4$—$CH_2$—); 1.64 (m, 2H, —$C_6H_4$—$CH_2$—$CH_2$—); 1.41 (t, J=7.2, 3H, $CH_3$—$CH_2$—O—); 1.27 (m, 24H, C$H_3$—$CH_2$—O—); 0.89 (t, J=6.4, 3H, C$H_3$—$(CH_2)_{14}$—$C_6H_4$—); m/z (EI) 389 (MH$^+$).

APPLICATION EXAMPLE 1

A clear UV-curable system based on polyurethane acrylate is prepared by mixing:
50.0 parts of a bifunctional urethane acrylate (Actilane® 200, Akcros)
25.0 parts of tripropylene glycol diacrylate (SR 306, Cray Valley)
15.0 parts of trimethylolpropane triacrylate TMPTA (UCB)
10.0 parts of dipentaerythritol pentaacrylate (SR 399, Cray Valley)

The samples were prepared by adding 2% of the photoinitiator.

The mixtures were applied to a white chipboard panel and irradiated using a UV processor (2×80 W/cm) at a belt speed of 3 m/min. A tack-free dry film with a thickness of approximately 50 μm is obtained.

30 minutes after cure, the pendulum hardness according to Koenig (DIN 53157) is measured. Surface energy of the coating is determined by measuring static water contact angle (θ) using a contact angle measuring system G10 from Krüss. The higher the value of the pendulum hardness measurement, the harder the cured surface. The higher the contact angle, the better the moisture resistance and scratch resistance.

| Initiator | pendulum hardness (sec) | water contact angle (θ) |
|---|---|---|
| Nuvopol (Methyloxobenzene acetate) | 132 | 68 |
| Nuvopol Dimer | 127 | 64 |
| Ex. 4 | 86 | 75 |
| Ex. 1 | 134 | 83 |

APPLICATION EXAMPLE 2

A clear dual-cure system based on polyurethanes is prepared by mixing:
21.1 parts of Desmophen® LS 2009/1, hydroxy-functional polyacrylate (Bayer AG)
32.3 parts of Roskydal® FWO 2518C, isocyanurate-based urethane acrylate 80% in butyl acetate (Bayer AG)
0.3 part of Baysilone® OL 17, flow improver, 10% in xylene (Bayer AG)
0.3 part of Modaflow® flow improver (Monsanto)
26.0 parts of 1-methoxy-2-propanol (Fluka Chemicals)
11.2 parts of Roskydal® FWO 2545 E urethane acrylate with isocyanate groups (BayerAG)

The samples were prepared by adding 2–3% of the photoinitiator, and to some extent light stabilizer and HALS (hindered amine light stabilizer) is used.

The mixtures were applied to white coil-coated aluminium, air-dried for 5 min. at room temperature and heated on a hotplate at 80° C. for 10 min. Irradiation is then carried out using a UV processor (2×120 W/cm) at a belt speed of 5 m/min. A tack-free dry film with a thickness of approximately 40 μm is obtained.

45 min. after cure, the pendulum hardness according to Koenig (DIN 53157) is measured. Surface energy of the coating is determined by measuring static water contact angle θ using a contact angle system G10 from Krüss. The higher the value of the pendulum hardness measurement, the harder the cured surface. The higher the contact angle, the better the moisture resistance and scratch resistance.

| Initiator | pendulum hardness (sec) | water contact angle θ |
|---|---|---|
| Nuvopol (Methyloxobenzene acetate) | 132 | 68 |
| Nuvopol Dimer | 127 | 64 |
| Ex. 4 | 55 | 88 |
| Ex. 1 | 52 | 92 |

What is claimed is:

1. A compound of the formula Ia, Ib or Ic

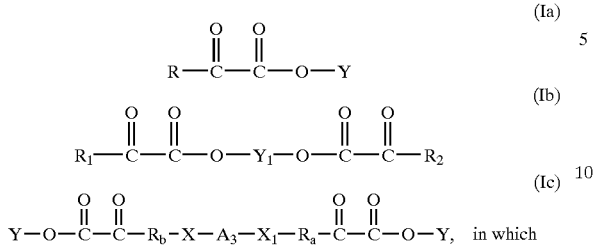

in which

R, $R_1$ and $R_2$ independently of one another are a radical of the formula II

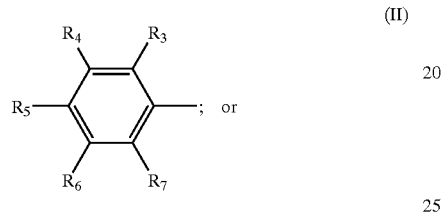

R, $R_1$ and $R_2$ are naphthyl, anthracyl, phenanthryl or a heterocyclic radical, the radicals naphthyl, anthracyl, phenanthryl and the heterocyclic radical being unsubstituted or substituted by A-X—, $A_1$-$X_1$—, $A_2$-$X_2$—, $C_1$–$C_8$alkyl, phenyl, $OR_8$, $SR_9$ and/or $NR_{10}R_{11}$, where the substituents $OR_8$, $SR_9$ and $NR_{10}R_{11}$ may form 5- or 6-membered rings via the radicals $R_8$, $R_9$, $R_{10}$ and/or $R_{11}$ with further substituents on the naphthyl, anthracyl or phenanthryl ring or on the heterocycle or with one of the carbon atoms of the naphthyl, anthracyl or phenanthryl ring or with one of the carbon atoms of the heterocycle;

with the proviso that at least one substituent A-X—, $A_1$-$X_1$— or $A_2$-$X_2$— is present in the radical R or in at least one of the radicals $R_1$ or $R_2$;

$R_3$, $R_4$, $R_5$, $R_6$ and $R_7$ independently of one another are hydrogen; A-X—, $A_1$-$X_1$—, $A_2$-$X_2$—; unsubstituted $C_1$–$C_{12}$alkyl or $C_1$–$C_{12}$alkyl substituted by OH, $C_1$–$C_4$alkoxy, phenyl, naphthyl, halogen, CN and/or —O(CO)$R_{12}$; or are $C_2$–$C_{12}$alkyl interrupted by one or more non-successive oxygen atoms; or $R_3$, $R_4$, $R_5$, $R_6$ and $R_7$ are halogen, $OR_8$, $SR_9$, $NR_{10}R_{11}$, unsubstituted or $C_1$–$C_4$alkyl- and/or $C_1$–$C_4$alkoxy-substituted phenyl, where the substituents $OR_8$, $SR_9$, $NR_{10}R_{11}$ may form 5- or 6-membered rings via the radicals $R_8$, $R_9$, $R_{10}$ and/or $R_{11}$ with further substituents on the phenyl ring or one of the carbon atoms of the phenyl ring;

with the proviso that at least one radical $R_3$, $R_4$, $R_5$, $R_6$ or $R_7$ is A-X—, $A_1$-$X_1$—, or $A_2$-$X_2$—;

$R_8$ and $R_9$ independently of one another are hydrogen; unsubstituted $C_1$–$C_{12}$alkyl or $C_1$–$C_{12}$alkyl substituted by OH, $C_1$–$C_4$alkoxy, phenyl, phenoxy and/or —O(CO)$R_{12}$; or are $C_2$–$C_{12}$alkyl interrupted by one or more non-successive oxygen atoms; or are unsubstituted phenyl, $C_3$–$C_6$alkenyl, cyclopentyl, cyclohexyl or naphthyl; or are $C_1$–$C_4$alkoxy-, phenyl- and/or $C_1$–$C_4$alkyl-substituted phenyl, $C_3$–$C_6$alkenyl, cyclopentyl, cyclohexyl or naphthyl;

$R_{10}$ and $R_{11}$ independently of one another are hydrogen; unsubstituted $C_1$–$C_{12}$alkyl or $C_1$–$C_{12}$alkyl substituted by OH, $C_1$–$C_4$alkoxy and/or phenyl; or are $C_2$–$C_{12}$alkyl interrupted by one or more non-successive oxygen atoms; or are phenyl, —(CO)$R_{12}$ or $SO_2R_{13}$; or $R_{10}$ and $R_{11}$, together with the nitrogen atom to which they are attached, form a 5-, 6- or 7-membered ring which is uninterrupted or interrupted by —O— or —$NR_{14}$—;

$R_{12}$ is $C_1$–$C_8$alkyl; unsubstituted phenyl or phenyl substituted by $C_1$–$C_4$alkyl and/or $C_1$–$C_4$alkoxy;

$R_{13}$ is $C_1$–$C_{12}$alkyl, unsubstituted phenyl or phenyl substituted by $C_1$–$C_4$alkyl;

$R_{14}$ is hydrogen; unsubstituted $C_1$–$C_8$alkyl; $C_1$–$C_8$alkyl substituted by OH or $C_1$–$C_4$alkoxy; unsubstituted phenyl; or phenyl substituted by OH, $C_1$–$C_4$alkyl or $C_1$–$C_4$alkoxy;

$R_a$ and $R_b$ independently of one another are phenylene, naphthylene, anthracylene, phenanthrylene or a divalent heterocyclic radical, these radicals being unsubstituted or substituted by A-X—, $A_1$-$X_1$—, $A_2$-$X_2$—, $C_1$–$C_8$alkyl, phenyl, $OR_8$, $SR_9$ and/or $NR_{10}R_{11}$, where the substituents $OR_8$, $SR_9$ and $NR_{10}R_{11}$ may form 5- or 6-membered rings via the radicals $R_8$, $R_9$, $R_{10}$ and/or $R_{11}$ with further substituents on the phenylene, naphthylene, anthracylene or phenanthrylene ring or on the divalent heterocycle or with one of the carbon atoms of the naphthylene, anthracylene or phenanthrylene ring or of the divalent heterocycle;

A, $A_1$ and $A_2$ independently of one another are a surface-active radical of the formula III

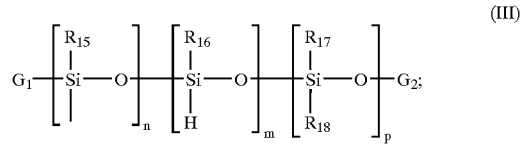

in which the units IIIa1, IIIa2, IIIb and/or IIIc

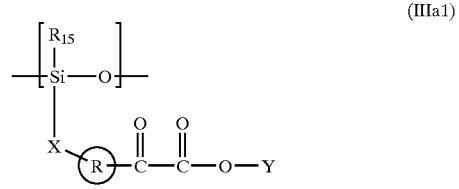

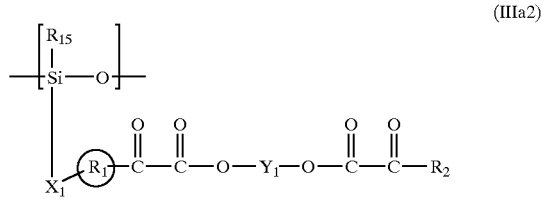

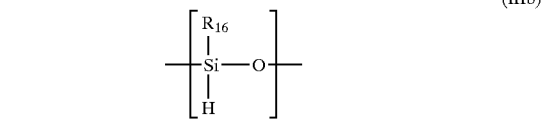

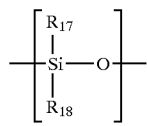
(IIIc)

are distributed randomly or in blocks and in which the circle is intended to show that an aromatic radical R or $R_1$ as defined above is a divalent radical and is substituted via the bridges X or $X_1$ with the corresponding silyl radical; or A, $A_1$ and $A_2$ are a surface-active radical $A_0$; where $A_0$ is $C_6$–$C_{30}$alkyl, $C_6$–$C_{30}$alkenyl, $C_6$–$C_{30}$alkynyl, $C_6$–$C_{30}$aralkyl, $C_6$–$C_{30}$alkyl-(CO)—, $C_6$–$C_{30}$alkenyl-(CO)—, $C_6$–$C_{30}$alkynyl-(CO)—, $C_6$–$C_{30}$aralkyl-(CO)—, $C_6$–$C_{30}$alkyl-Si($R_{15}$)($R_{16}$)—, $C_6$–$C_{30}$alkenyl-Si($R_{15}$)($R_{16}$)—, $C_6$–$C_{30}$alkynyl-Si($R_{15}$)($R_{16}$)—, these radicals being unsubstituted or substituted by OH, $C_1$–$C_4$alkoxy, phenyl, naphthyl, halogen, CN, $SR_9$, $NR_{10}R_{11}$ and/or —O(CO)$R_{12}$ and these radicals being uninterrupted or interrupted by one or more —O—, —S— or —$NR_{14}$—;

n is a number from 1 to 1000 or, if the siloxane starting material is a mixture of oligomeric siloxanes, n may alternatively be less than 1 but greater than 0;

m is a number from 0 to 100;

p is a number 0–10 000;

$A_3$ is a radical of the formula III in which n is from 2 to 1000; or $A_3$ is a surface-active radical $A_4$, where $A_4$ is $C_6$–$C_{30}$alkylene, $C_6$–$C_{30}$alkenylene, $C_6$–$C_{30}$alkynylene, $C_6$–$C_{30}$aralkylene, $C_6$–$C_{30}$alkylene-(CO)—, $C_6$–$C_{30}$alkenylene-(CO)—, $C_6$–$C_{30}$alkynylene(CO)—, $C_6$–$C_{30}$aralkylene-(CO)—, —(CO)—$C_6$–$C_{30}$alkylene-(CO)—, —(CO)—$C_6$–$C_{30}$alkenylene-(CO)—, —(CO)—$C_6$–$C_{30}$alkynylene-(CO)—, —(CO)—$C_6$–$C_{30}$aralkylene-(CO)—, $C_6$–$C_{30}$alkylene-Si($R_{15}$)($R_{16}$), $C_6$–$C_{30}$alkenylene-Si($R_{15}$)($R_{16}$)—, $C_6$–$C_{30}$alkynylene-Si($R_{15}$)($R_{16}$)—, —Si($R_{15}$)($R_{16}$)—$C_6$–$C_{30}$alkylene-Si($R_{15}$)($R_{16}$)—, —Si($R_{15}$)($R_{16}$)—$C_6$–$C_{30}$alkenylene-Si($R_{15}$)($R_{16}$)—, —Si($R_{15}$)($R_{16}$)—$C_6$–$C_{30}$alkynylene-Si($R_{15}$)($R_{16}$)—, these radicals being unsubstituted or substituted by OH, $C_1$–$C_4$alkoxy, phenyl, naphthyl, halogen, CN, $SR_9$, $NR_{10}R_{11}$ and/or —O(CO)$R_{12}$ and these radicals being uninterrupted or interrupted by one or more —O—, —S— or —$NR_{14}$—;

$G_1$ is $C_1$–$C_{18}$alkyl or a radical of the formula

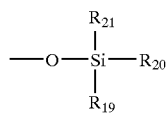

$G_2$ is $C_1$–$C_{18}$alkyl or a radical of the formula

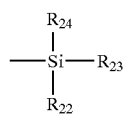

with the proviso that, if $G_2$=alkyl, the radical $G_2$ is attached directly to the silicon atom without an oxygen bridge; or $G_1$ and $G_2$ together are a single bond;

$R_{15}$, $R_{16}$, $R_{17}$, $R_{19}$, $R_{20}$, $R_{21}$, $R_{22}$, $R_{23}$ and $R_{24}$ independently of one another are $C_1$–$C_{18}$alkyl, phenyl, $C_2$–$C_6$-hydroxyalkyl, $C_2$–$C_6$-aminoalkyl or $C_5$–$C_8$cycloalkyl;

$R_{18}$ is unsubstituted $C_1$–$C_{18}$alkyl, $C_5$–$C_8$cycloalkyl; or is $C_1$–$C_{18}$alkyl substituted by hydroxyl, $C_1$–$C_{12}$alkoxy, halogen, $C_3$–$C_8$cycloalkyl and/or N($R_{10}$)($R_{11}$); or is unsubstituted phenyl or phenyl substituted by $C_1$–$C_{12}$alkyl, $C_1$–$C_{12}$alkoxy, halogen, hydroxyl and/or N($R_{10}$)($R_{11}$);

X, $X_1$ and $X_2$ if A, $A_1$, $A_2$ and $A_3$ are a radical of the formula III, independently of one another are a single bond, $C_1$–$C_{10}$alkylene, $C_2$–$C_{10}$alkenylene, $C_2$–$C_{10}$alkynylene, —(CH$_2$)$_a$—O—, —O—(CH$_2$)$_a$—, —O—(CH$_2$)$_a$—O—, —(CH$_2$)$_a$—O—(CH$_2$)$_b$—, —(CH$_2$)$_a$—O—(CH$_2$)$_b$—O—, —(CH$_2$)$_a$—$NR_{14}$—(CH$_2$)$_b$—, —(CH$_2$)$_a$—$NR_{14}$—, —(CH$_2$)$_a$—O—(CH$_2$)$_b$—$NR_{14}$—(CH$_2$)$_c$—, —(CH$_2$)$_a$—O—(CH$_2$)$_b$—$NR_{14}$—, —($C_2$–$C_{10}$alkenylene)-O—(CH$_2$)$_a$—, —($C_2$–$C_{10}$alkenylene)-O—, —($C_2$–$C_{10}$alkynylene)-O—(CH$_2$)$_a$—, —($C_2$–$C_{10}$alkynylene)-O—, —($C_2$–$C_{10}$alkenylene)-O—(CH$_2$)$_a$—O—, —($C_2$–$C_{10}$alkynylene)-O—(CH$_2$)$_a$—O—, —($C_2$–$C_{10}$alkenylene)-$NR_{14}$—(CH$_2$)$_a$—, —($C_2$–$C_{10}$alkenylene)-$NR_{14}$—, —($C_2$–$C_{10}$alkynylene)-$NR_{14}$—(CH$_2$)$_a$—, —($C_2$–$C_{10}$alkynylene)-$NR_{14}$—, —($C_2$–$C_{10}$alkenylene)-O—(CH$_2$)$_a$—$NR_{14}$— or —($C_2$–$C_{10}$alkynylene)-O—(CH$_2$)$_a$—$NR_{14}$—; and X, $X_1$ and $X_2$ if A, $A_1$ or $A_2$ have the definition of $A_0$ or $A_3$ has the definition of $A_4$, independently of one another are a single bond, —O—, —S— or —$NR_{14}$—;

a, b and c independently of one another are a number from 0 to 10; but with the proviso that they are at least 1 if the methylene group in question is between two oxygen atoms or between one oxygen atom and one nitrogen atom;

Y is hydrogen; unsubstituted $C_1$–$C_{20}$alkyl or $C_1$–$C_{20}$alkyl substituted by a group A-X—; unsubstituted $C_2$–$C_{18}$alkenyl or $C_2$–$C_{18}$alkenyl substituted by a group A-X—; unsubstituted $C_2$–$C_{18}$alkynyl or $C_2$–$C_{18}$alkynyl substituted by a group A-X—; or Y is phenyl, naphthyl, anthracyl or phenanthryl, these radicals being unsubstituted or substituted by one or more groups A-X— and/or $C_1$–$C_{12}$alkyl; or Y is $C_1$–$C_4$alkyl which is substituted by phenyl, naphthyl, anthracyl, phenanthryl and if desired additionally by a group A-X—; or Y is the salt radical of the respective glyoxalic acid;

$Y_1$ is unsubstituted $C_1$–$C_{12}$alkylene or $C_1$–$C_{12}$alkylene substituted by a group $A_1$-$X_1$—; unsubstituted $C_4$–$C_8$alkenylene or $C_4$–$C_8$alkenylene substituted by a group $A_1$-$X_1$—; unsubstituted $C_4$–$C_8$alkynyiene or $C_4$–$C_8$alkynylene substituted by a group $A_1$-$X_1$—; unsubstituted cyclohexylene or cyclohexylene substituted by a group $A_1$-$X_1$—; $C_4$–$C_{40}$alkylene which is interrupted one or more times by —O—, —S— or —$NR_{25}$— and which is unsubstituted or substituted by a group $A_1$-$X_1$—; or $Y_1$ is unsubstituted phenylene or phenylene substituted by a group $A_1$-$X_1$—; or $Y_1$ is a radical of the formula V, VI, VII, VIII, IX, X, XI, XII, XIII, XIV or XV

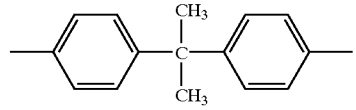 (V)

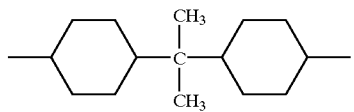 (VI)

—CH$_2$CH(OH)CH$_2$O—Y$_2$—OCH$_2$CH(OH)CH$_2$— (VII)
—CH$_2$CH(OH)CH$_2$— (VIII)

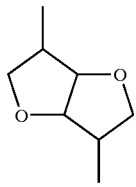 (IX)

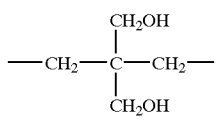 (X)

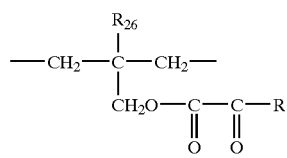 (XI)

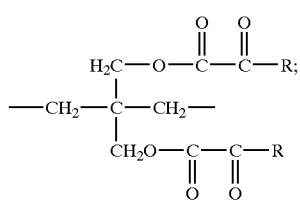 (XII)

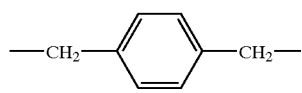 (XIII)

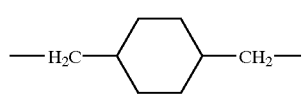 (XIV)

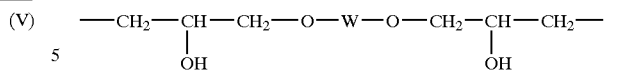

where the radicals of the formula V, VI, VII, VIII, IX, X, XI, XII, XIII, XIV or XV are unsubstituted or substituted by a group A$_1$—X$_1$—;
Y$_2$ is Y$_1$ with the exception of the formula VII;
R$_{25}$ is hydrogen, C$_1$–C$_{12}$alkyl or phenyl; and
R$_{26}$ is hydrogen, CH$_2$OH or C$_1$–C$_4$alkyl;
W is C$_1$–C$_{10}$alkylene; and
R is as defined above.

2. A compound of the formula Ia, Ib or Ic according to claim 1, wherein

R, R$_1$ and R$_2$ independently of one another are a radical of the formula II indicated above, or R, R$_1$ and R$_2$ are naphthyl, the naphthyl radical being unsubstituted or substituted by A-X—, A$_1$-X$_1$—, A$_2$-X$_2$—, C$_1$–C$_8$alkyl, phenyl or OR$_8$, with the proviso that there is at least one substituent A-X—, A$_1$-X$_1$— or A$_2$-X$_2$— in the radical R or in at least one of the radicals R$_1$ or R$_2$;

R$_3$, R$_4$, R$_5$, R$_6$ and R$_7$ independently of one another are hydrogen; A-X—, A$_1$-X$_1$—, A$_2$-X$_2$—;
unsubstituted C$_1$–C$_{12}$alkyl; or
C$_2$–C$_{12}$alkyl which is interrupted by one or more non-successive oxygen atoms; or R$_3$, R$_4$, R$_5$, R$_6$ and R$_7$ are halogen, OR$_8$ or unsubstituted phenyl,
with the proviso that at least one radical R$_3$, R$_4$, R$_5$, R$_6$ or R$_7$ is A-X—, A$_1$-X$_1$— or A$_{2-X2}$—;

R$_8$ is hydrogen or unsubstituted C$_1$–C$_{12}$alkyl; or is
C$_2$–C$_{12}$alkyl which is interrupted by one or more non-successive oxygen atoms; or is
phenyl, C$_3$–C$_6$alkenyl, cyclopentyl or cyclohexyl, these radicals being unsubstituted;

R$_a$ and R$_b$ independently of one another are phenylene or naphthylene, these radicals being unsubstituted or substituted by A-X—, A$_1$-X$_1$—, A$_2$-X$_2$—, C$_1$–C$_8$alkyl, phenyl or OR$_8$, A, A$_1$ and A$_2$ independently of one another are a surface-active radical of the formula III indicated above; or A, A$_1$ and A$_2$ are a surface-active radical A$_0$; where A$_0$ is C$_6$–C$_{30}$alkyl, C$_6$–C$_{30}$aralkyl, C$_6$–C$_{30}$alkyl-(CO)—, C$_6$–C$_{30}$aralkyl-(CO)—, C$_6$–C$_{30}$alkyl-Si(R$_{15}$)(R$_{16}$)—, these radicals being unsubstituted or substituted by F;

n is as defined in claim 1;
m is as defined in claim 1;
p is as defined in claim 1;

A$_3$ is a radical of the formula III in which n has a value from 2 to 100; or A$_3$ is a surface-active radical A$_4$; where A$_4$ is
C$_6$–C$_{30}$alkylene, C$_6$–C$_{30}$aralkylene, C$_6$–C$_{30}$alkylene-(CO)—,
C$_6$–C$_{30}$aralkylene-(CO)—, —(CO)—C$_6$–C$_{30}$alkylene-(CO)—,
—(CO)—C$_6$–C$_{30}$aralkylene-(CO)—, C$_6$–C$_{30}$alkylene-Si(R$_{15}$)(R$_{16}$)—,
—Si(R$_{15}$)(R$_{16}$)—C$_6$–C$_{30}$alkylene-Si(R$_{15}$)(R$_{16}$)—,
these radicals being unsubstituted or substituted by F;

G$_1$ is as defined in claim 1;
G$_2$ is as defined in claim 1;
R$_{15}$, R$_{16}$, R$_{17}$, R$_{19}$, R$_{20}$, R$_{21}$, R$_{22}$, R$_{23}$ and R$_{24}$ independently of one another are C$_1$–C$_{18}$alkyl or phenyl;

$R_{18}$ is unsubstituted $C_1$–$C_{18}$alkyl or phenyl;

X, $X_1$ and $X_2$, if A, $A_1$, $A_2$ and $A_3$ are a radical of the formula III, are independently of one another $C_1$–$C_{10}$alkylene,
—$(CH_2)_a$—O—, —O—$(OH_2)_a$—, —O—$(CH_2)_a$—O—,
—$(CH_2)_a$—O—$(CH_2)_b$—; —$(CH_2)_a$—O—$(CH_2)_b$—O—, —$(CH_2)_a$—$NR_{14}$—$(CH_2)_b$—,
—$(CH_2)_a NR_{14}$—, —$(CH_2)_a$—O—$(CH_2)_b$—$NR_{14}$—$(CH_2)_c$—,
—$(CH_2)_a$—O—$(CH_2)_b$—$NR_{14}$—; and X, $X_1$ and $X_2$, if A, $A_1$ or $A_2$ have the definition of $A_0$ or $A_3$ has the definition of $A_4$, are independently of one another a single bond, —O—, —S— or —$NR_{14}$—;

$R_{14}$ is as defined in claim 1;

a, b and c independently of one another are a number from 0 to 3; with the proviso that they are, however, at least 1 if the methylene group in question is between two oxygen atoms or one oxygen atom and one nitrogen atom;

Y is $C_1$–$C_{20}$alkyl which is unsubstituted or substituted by a group A-X—; or Y is phenyl or naphthyl, these radicals being unsubstituted or substituted by one or more groups A-X— and/or $C_1$–$C_{12}$alkyl; or Y is $C_1$–$C_4$alkyl which is substituted by phenyl, naphthyl, anthracyl, phenanthryl and, if desired, additionally by a group A-X—;

$Y_1$ is $C_1$–$C_{12}$alkylene which is unsubstitued or substituted by a group $A_1$-$X_1$—;
cyclohexylene which is unsubstituted or substituted by a group $A_1$-$X_1$—, $C_4$–$C_{40}$alkylene which is interrupted one or more times by —O—, —S— or —$NR_{25}$— and which is unsubstituted or substituted by a group $A_1$-$X_1$—; or
$Y_1$ is phenylene which is unsubstituted or substituted by a group $A_1$-$X_1$—; or $Y_1$ is a radical of the formulae V, VI, VII, VIII, IX, X, XI, XII, XIII, XIV or XV indicated above,
the radicals of the formula V, VI, VII, VIII, IX, X, XI, XII, XIII, XIV or XV being unsubstituted or substituted by a group $A_1$-$X_1$—;

$Y_2$ is $Y_1$ with the exception of the formula VII.

3. A compound of the formula Ia, Ib or Ic according to claim 2, wherein

R, $R_1$ and $R_2$ independently of one another are a radical of the formula II indicated above, $R_3$, $R_4$, $R_5$, $R_6$ and $R_7$ independently of one another are hydrogen or A-X—, $A_1$-$X_1$—, $A_2$-$X_2$—;
with the proviso that at least one radical $R_3$, $R_4$, $R_5$, $R_6$ or $R_7$ is A-X—, $A_1$-$X_1$— or $A_2$-$X_2$—;

$R_a$ and $R_b$ are phenylene,

A, $A_1$ and $A_2$ independently of one another are a surface-active radical of the formula III indicated above; or A, $A_1$ and $A_2$ are a surface-active radical $A_0$, where $A_0$ is $C_6$–$C_{30}$alkyl or $C_6$–$C_{30}$alkyl-(CO)—, these radicals being unsubstituted or substituted by F;

n is an integer 1–100;

m is an integer 0–100;

p is an integer 1–100;

$A_3$ is a radical of the formula III in which n has a value from 2 to 100; or $A_3$ is a surface-active radical $A_4$, where $A_4$ is $C_6$–$C_{30}$alkylene or —(CO)— $C_6$–$C_{30}$alkylene-(CO)—, these radicals being unsubstituted or substituted by F;

$G_1$ is methyl or —O—Si($R_{19}$, $R_{20}$, $R_{21}$);

$G_2$ is methyl or —Si($R_{22}$, $R_{23}$, $R_{24}$), with the proviso that, if $G_2$ is methyl, the radical $G_2$ is attached directly to the silicon atom without an oxygen bridge;

$R_{15}$, $R_{16}$, $R_{17}$, $R_{18}$, $R_{19}$, $R_{20}$, $R_{21}$, $R_{22}$, $R_{23}$ and $R_{24}$ independently of one another are methyl or phenyl;

X, $X_1$ and $X_2$, if A, $A_1$, $A_2$ and $A_3$ are a radical of the formula III, are independently of one another $C_1$–$C_{10}$alkylene,
or —$(CH_2)_a$—O—; and X, $X_1$ and $X_2$, if A, $A_1$ or $A_2$ have the definition of $A_0$ or $A_3$ has the definition of $A_4$, are independently of one another a single bond or —O—;

a is a number from 1 to 3;

Y is unsubstituted $C_1$–$C_{20}$alkyl;

$Y_1$ is unsubstituted $C_1$–$C_{12}$alkylene interrupted one or more times by —O—; or
$Y_1$ is unsubstituted phenylene;
or $Y_1$ is a radical of the formulae V, VI, VII, VIII, IX, X, XI, XII, XIII, XIV or XV indicated above;

$Y_2$ is $Y_1$ with the exception of the formula VII;

$R_{25}$ is as defined in claim 1.

4. A composition comprising (A) at least one ethylenically unsaturated free-radically photopolymerizable compound; and (B) at least one surface-active photoinitiator of the formula Ia, Ib or Ic.

5. A composition comprising (A) at least one ethylenically unsaturated free-radically photopolymerizable compound;

(B) at least one surface-active photoinitiator of the formula Ia, Ib or Ic, and (C) at least one thermally crosslinkable compound.

6. A composition according to claim 4, comprising in addition to components (A) and (B), or (A), (B) and (C), further additives (D) and/or additional photoinitiators (E).

7. A process for producing coatings having stable scratch-resistant surfaces, in which (1) a photocurable formulation comprising
  (A) an ethylenically unsaturated polymerizable compound; and
  (B) a photoinitiator;
is prepared;

(2) this formulation is applied to a substrate; and (3) the formulation is cured either
  only by exposure to electromagnetic radiation with a wavelength ranging from 200 nm into the IR region, or
  by exposure to electromagnetic radiation with a wavelength ranging from 200 nm into the IR region and prior, simultaneous and/or subsequent exposure to heat;

wherein the formulation comprises as photoinitiator (B) at least one surface-active photoinitiator of the formula Ia, Ib or Ic, according to claim 1 which accumulates at the surface of the formulation.

8. A process according to claim 7, wherein the photocurable formulation comprises as a further component at least one thermally crosslinkable compound (C) and is cured by exposure to electromagnetic radiation with a wavelength ranging from 200 nm into the IR region and prior, simultaneous and/or subsequent exposure to heat.

9. A process according to claim 8, wherein the thermally crosslinkable compound (C) is a binder based on a polyacrylate with melamine or melamine derivative, or a system based on a polyacrylate polyol and/or polyester polyol with an unblocked polyisocyanate or polyisocyanurate.

10. A process according to claim 7 for preparing pigmented and unpigmented paints and varnishes, powder coating materials, gel coats, composite materials or glass fibre cable coatings.

11. A method of causing a photoinitiator to accumulate at the surface of coatings comprising ethylenically unsaturated photopolymerizable compounds, which comprises adding a surface-active photoinitiator of the formula Ia, Ib or Ic according to claim 1 to the photopolymerizable mixture comprising the ethylenically unsaturated photopolymerizable compounds.

12. A substrate, wherein the substrate is coated on at least one surface of the substrate with a composition according to claim 4 and cured.

13. A composition according to claim 5, comprising in addition to components (A) and (B), or (A), (B) and (C), further additives (D) and/or additional photoinitiators (E).

14. A substrate, wherein the substrate is coated on at least one surface with a composition according to claim 5 and cured.

* * * * *